United States Patent
Tang et al.

(10) Patent No.: US 10,947,261 B2
(45) Date of Patent: Mar. 16, 2021

(54) TETRAVALENT PLATINUM COMPOUND-BICYCLIC DOUBLE-BOND-CONTAINING AMPHIPHILIC POLYMER PRODRUG, NANO-MICELLE, PREPARATION METHOD AND APPLICATION THEREOF

(71) Applicant: ANHUI UNIVERSITY, Hefei (CN)

(72) Inventors: Rupei Tang, Hefei (CN); Liefeng Hu, Hefei (CN)

(73) Assignee: ANHUI UNIVERSITY, Hefei (CN)

( * ) Notice: Subject to any disclaimer, the term of this patent is extended or adjusted under 35 U.S.C. 154(b) by 69 days.

(21) Appl. No.: 16/476,080

(22) PCT Filed: Dec. 29, 2017

(86) PCT No.: PCT/CN2017/119631
§ 371 (c)(1),
(2) Date: Jul. 4, 2019

(87) PCT Pub. No.: WO2019/127297
PCT Pub. Date: Jul. 4, 2019

(65) Prior Publication Data
US 2019/0345181 A1  Nov. 14, 2019

(30) Foreign Application Priority Data

Dec. 27, 2017  (CN) .......................... 201711448846.1

(51) Int. Cl.
*A61K 45/06* (2006.01)
*C07F 15/00* (2006.01)
*C08G 65/26* (2006.01)

(52) U.S. Cl.
CPC ...... *C07F 15/0093* (2013.01); *C08G 65/2603* (2013.01); *A61K 45/06* (2013.01)

(58) Field of Classification Search
CPC ............ C07F 15/0093; C08G 65/2603; C08G 65/2606; A61K 45/06; A61K 9/1075; A61K 33/243; A61K 33/24; A61P 35/00
See application file for complete search history.

(56) References Cited

U.S. PATENT DOCUMENTS

2012/0164230 A1  6/2012  Feazell et al.

FOREIGN PATENT DOCUMENTS

| CN | 102416181 A | 4/2012 |
| CN | 103804339 A | 5/2014 |

(Continued)

OTHER PUBLICATIONS

Wang R et al in Journal of Materials Chemistry, vol. 22, pp. 25453-25462, 2012 (Year: 2012).*

*Primary Examiner* — Gollamudi S Kishore
(74) *Attorney, Agent, or Firm* — Bayramoglu Law Offices LLC

(57) ABSTRACT

A tetravalent platinum compound-bicyclic double-bond-containing amphiphilic polymer prodrug, which has the structure as shown in formula (I):

when m=1, (Continued)

represents

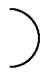

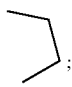

;

when m=0, represents

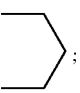

;

R represents —CH$_3$ or —CH$_2$CH$_3$; L$_1$ and L$_2$ independently represent Cl, N$_3$, NO$_3$,

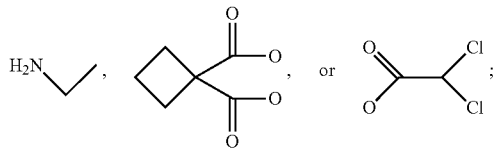

and n is from 10 to 80. A preparation method of the prodrug is also disclosed. The method includes a step of reacting an axially dihydroxy-coordinated tetravalent platinum compound with a bicyclic double-bond-containing orthoester precursor. In addition, a nano-micelle formed by the prodrug and an application thereof are further disclosed. The amphiphilic polymer prodrug and the micelle formed therefrom have pH hypersensitivity and reduction dual responsiveness.

18 Claims, 15 Drawing Sheets

(56) References Cited

FOREIGN PATENT DOCUMENTS

| CN | 103804684 | * | 5/2014 |
|----|-----------|---|--------|
| CN | 103804684 | A | 5/2014 |
| CN | 104353083 | A | 2/2015 |

* cited by examiner

TETRAVALENT PLATINUM COMPOUND-BICYCLIC DOUBLE-BOND-CONTAINING AMPHIPHILIC POLYMER PRODRUG, NANO-MICELLE, PREPARATION METHOD AND APPLICATION THEREOF

CROSS REFERENCE TO THE RELATED APPLICATIONS

This application is the national phase entry of International Application No. PCT/CN2017/119631, filed on Dec. 29, 2017, which is based upon and claims priority to Chinese Patent Application No. 201711448846.1, filed on Dec. 27, 2017, the entire contents of which are incorporated herein by reference.

TECHNICAL FIELD

The present invention relates to the technical field of biomedicine, and particularly to a tetravalent platinum compound-bicyclic double-bond-containing amphiphilic polymer prodrug, a nano-micelle, a preparation method and an application thereof.

BACKGROUND

As one of the major diseases threatening human health, cancer is actually the most common type of malignant tumors. The incidence and fatality rate of cancer are constantly increasing, and the methods for treating tumors are constantly being updated. In recent years, methods that are widely studied for treating tumors include non-traditional methods such as photothermal therapy, immunotherapy, etc., and the therapeutic effects thereof are remarkable. Most of the photothermal therapies rely on photosensitizers to convert tumor dissolved oxygen into reactive oxygen to treat tumors. However, the hypoxia environment inside tumors greatly limits the application of the photothermal therapy in treating tumors. Moreover, the laser used in the photothermal therapy also causes certain damage to the body, which causes the functional disorder inside the body. Immunotherapy aims to prevent the recurrence of malignant tumors and does not essentially cure the tumors. Moreover, exogenous immune substances (such as proteins, polypeptides, DNA, RNA and analogues thereof or immune factors) used in the immunotherapy may cause damage to the body due to the immunogenicity of the body. In addition, immunotherapy still faces great challenges due to the complicated operation process and high treatment expense of the current immunotherapy. Due to the above-mentioned drawbacks of the non-traditional methods, traditional methods for treating cancer still have an irreplaceable status, and the traditional methods mainly include surgical resection, radiotherapy, and chemotherapy. Among them, chemotherapy, abbreviation of chemical medicine therapy, is a treatment method that uses chemical medicines to prevent the proliferation, infiltration and metastasis of cancer cells and finally kill cancer cells, which is particularly important in cancer treatment. However, in traditional chemotherapy, small molecule anticancer drugs, such as doxorubicin, cisplatin (CDDP), camptothecin, paclitaxel, 5-fluorouracil, etoposide, bleomycin, etc., are often used. Among these anticancer drugs, cisplatin accounts for nearly 50% of clinical chemotherapy drugs in recent years due to the remarkable effects on the treatments of various tumors, such as tumors of the head, neck, cervix, testis, uterus, and especially testicular tumors. Although cisplatin and other small molecule anticancer drugs are widely used in clinical practice, they often have shortcomings such as rapid metabolism, short half-life, low concentration in blood, and no tumor targeting ability, so that very few drugs can actually reach at the tumor site in the process of treatment. Therefore, multiple administrations are needed to increase the concentration of the drug reaching at the tumor site, so as to achieve a better therapeutic effect, but a long-term administration will inevitably cause the cells to develop drug resistance.

In recent years, a large number of studies on anticancer drugs focus on the preparation of delivery systems that can transiently inactivate drugs, including liposomes, micelles, polymers, and inorganic nanoparticles. All non-targeted nano-drug carriers can be well enriched in the tumor site through the enhanced permeability and retention effect (EPR) of solid tumors. However, due to the self-clearance mechanism of the body, the therapeutic effect of the drug delivery system is largely limited.

In order to overcome the above-mentioned drawbacks of anticancer drugs, the research hotspots mainly focus on the preparation of nano-drug carriers with high stability that can circulate in the blood circulation for a relatively long time, and the preparation of nano-drug carriers with high loading capacity and remarkable therapeutic effects. Therefore, PEG nano-drug carriers and nano-drug carriers of prodrug have been widely studied and applied. Based on many advantages of cisplatin, for example, the treatment effect on tumor therapy is remarkable, the half-life can be regulated with potential changes, and the chlorine element of cisplatin also provides a certain targeting ability for cisplatin to enter into tumor cells, nano-drug carriers of tetravalent platinum (Pt) prodrugs have also become a hotspot in the research of anti-tumor drugs. The advantages of the nano-drug carriers of Pt (IV) prodrugs are mainly as follows. (1) The toxicity of a relatively high dose of tetravalent platinum polymer is even lower than that of a relatively low dose of cisplatin, which can eliminate the toxic side effects caused by cisplatin. (2) Prodrug polymers can improve the drug utilization rate, thereby increasing the drug concentration at the tumor site and achieving a better tumor therapeutic effect. (3) The nano-drug controlled release carrier formed by the prodrug polymer can protect the activity of the drug and improve the stability of the drug. (4) The circulation time of the drug in the blood is prolonged, which facilitates the accumulation of the drug at the tumor site; and the number of administrations is reduced, which alleviates the suffering of the patient. (5) The slow drug release reduces the body's antagonistic effect on the drugs, thereby improving the effectiveness and safety of the drugs. (6) Drugs can be aggregated at the tumor site by both active targeting and passive targeting manners. (7) The synergistic effect of the reduced bivalent cisplatin and the tumor-treating reagents can significantly enhance the therapeutic effect, and one or more anti-tumor drugs, immune factors, photosensitizers, interference factors, etc., can be loaded by the carriers. (8) There is a certain probability of curing the tumors, and therefore human's life is greatly prolonged.

Among many nano-drug controlled release carriers, nano-drug carriers with environmental sensitivity have been widely studied. Specifically, in the study of pH-sensitive drug carriers, due to the higher acid sensitivity of the ortho ester bond compared with other acid-sensitive chemical bonds such as acetal, ketal, vinyl ether, etc., the degradation rate of the orthoester can be regulated by adjusting the molecular weight and hydrophobicity of the polyorthoester, thereby adjusting the release rate of the drugs. Therefore, the ortho ester bond has attracted much attention. In the study of reduction-sensitive nano-drug carriers, once the tetravalent platinum compounds enter the tumor cells, the tetravalent platinum compounds will be quickly reduced to the divalent cisplatin original drugs, so as to achieve the tumor therapeutic effect faster and more efficiently. Based on the above considerations, the present invention aims to produce a novel nano-drug formulation of polymer prodrug capable of completely curing tumors through the regulation of pH-sensitive bonds and high content of reducible tetravalent platinum.

SUMMARY

The technical problem to be solved by the present invention is to provide a tetravalent platinum compound-bicyclic double-bond-containing amphiphilic polymer prodrug having pH hypersensitivity and reduction dual responsiveness, a nano-micelle, a preparation method and an application thereof.

The technical solutions of the present invention for solving the above technical problems are as follows.

In one aspect, a tetravalent platinum compound-bicyclic double-bond-containing amphiphilic polymer prodrug is provided, which has the structure as shown in formula (I):

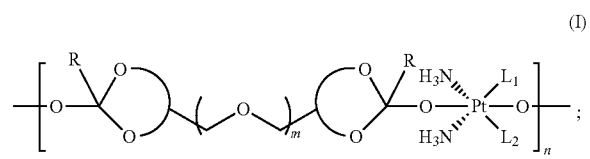
(I)

wherein, when m=1, represents

;

when m=0, represents

;

R represents —$CH_3$ or —$CH_2CH_3$; $L_1$ and $L_2$ independently represent Cl, $N_3$, $NO_3$,

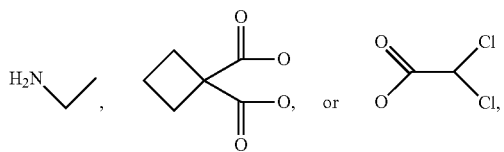

etc.; and n is from 10 to 80.

Preferably, the tetravalent platinum compound-bicyclic double-bond-containing amphiphilic polymer prodrug has the following structure:

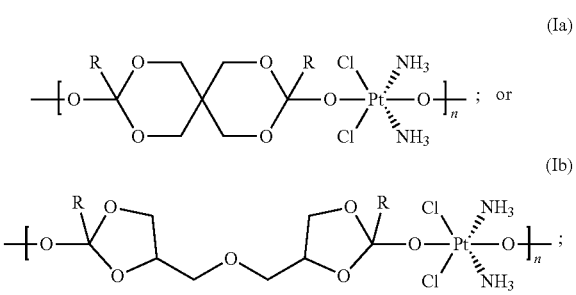

in the formula (Ia) and the formula (Ib), R represents —$CH_3$ or —$CH_2CH_3$, and n is from 10 to 80.

A method of preparing the above-mentioned tetravalent platinum compound-bicyclic double-bond-containing amphiphilic polymer prodrug is further provided. The method includes the step of reacting an axially dihydroxy-coordinated tetravalent platinum compound (oxoplatin) as shown in formula (II) with a bicyclic double-bond-containing orthoester precursor as shown in formula (III). The reaction equation is as follows:

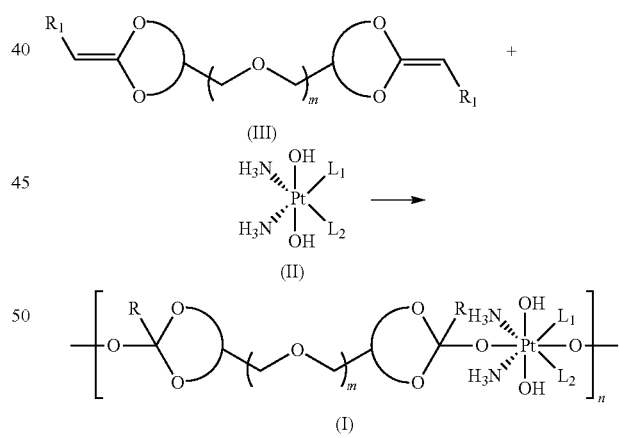

in the formula (II), $L_1$ and $L_2$ independently represent Cl, $N_3$, $NO_3$,

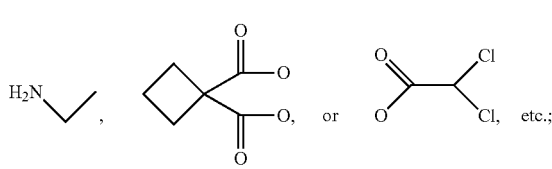

etc.;

in the formula (III), when m=1, represents

![structure]

;

when m=0, represents

![structure]

;

R₁ represents —H or —CH₃; and in the formula (I), when m=1, represents

![structure]

;

when m=0, represents

![structure]

;

R represents —CH₃ or —CH₂CH₃; L₁ and L₂ independently represent Cl, N₃, NO₃, $$H_2N\diagup\diagdown,\quad \text{(cyclobutane-1,1-dicarboxylate)},\quad \text{or}\quad \text{ClCH}_2\text{C(O)Cl},$$

etc.; and n is from 10 to 80.

Preferably, the above-mentioned method of preparing the tetravalent platinum compound-bicyclic double-bond-containing amphiphilic polymer prodrug includes the following steps: mixing the axially dihydroxy-coordinated tetravalent platinum compound and the bicyclic double-bond-containing orthoester precursor to obtain a mixture; then, adding p-toluenesulfonamide dissolved in a solvent to the mixture; finally, adding dimethyl sulfoxide and performing a reaction under a nitrogen protection; and then obtaining the tetravalent platinum compound-bicyclic double-bond-containing amphiphilic polymer prodrug after the reaction is terminated.

Preferably, the bicyclic double-bond-containing orthoester precursor is selected from the group consisting of 4,4-dimethoxy-bis-(2-methyl-1,3-dioxolane) (OMMD), 3,9-dimethylene -2,4,8,10-tetraoxaspiro[5.5]undecane (DMTU), (Z)-2-ethylidene-4-[(E)-2-ethylidene-1,3-dioxolan-4-yl-methoxy-methyl]-1,3-dioxolane (EEDMMD), and 3,9-diethylene-2,4,8,10-tetraoxaspiro-undecane (DETOSU).

Preferably, a molar ratio of the axially dihydroxy-coordinated tetravalent platinum compound to the bicyclic double-bond-containing orthoester precursor and to the p-toluenesulfonamide is 1:1:2‰.

Preferably, the reaction process is a stirring reaction at 30° C. to 60° C. for 24 h to 72 h.

Preferably, a step of terminating the reaction is dropwise adding triethylamine.

Preferably, in the p-toluenesulfonamide dissolved in the solvent, the solvent is dimethyl sulfoxide or dimethylformamide.

Preferably, a reaction equation for a preparation of the tetravalent platinum compound-bicyclic double-bond-containing amphiphilic polymer prodrug shown in formula (Ia) is as follows:

[Reaction scheme showing compound (IIIa): bicyclic orthoester with R₁ groups + compound (IIa): HO—Pt(Cl)₂(NH₃)₂—OH, with DMSO/p-TSA, yielding polymer (Ia) with repeating units containing Pt(Cl)₂(NH₃)₂ centers, n repeat units]

wherein, R₁ represents —H or —CH₃, R represents —CH₃ or —CH₂CH₃, and n is from 10 to 80.

A reaction equation for a preparation of the tetravalent platinum compound-bicyclic double-bond-containing amphiphilic polymer prodrug shown in formula (Ib) is as follows:

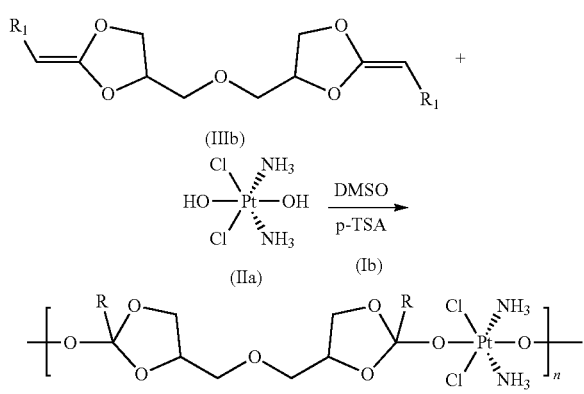

wherein, $R_1$ represents —H or —$CH_3$, R represents —$CH_3$ or —$CH_2CH_3$, and n is from 10 to 80.

In another aspect, a nano-micelle formed by the above-mentioned tetravalent platinum compound-bicyclic double-bond-containing amphiphilic polymer prodrug is provided.

A method of preparing the above-mentioned nano-micelle is further provided. The method includes the following steps: under light-proof conditions, placing the tetravalent platinum compound-bicyclic double-bond-containing amphiphilic polymer prodrug in a dialysis bag with a molecular weight cutoff value of 3500 for performing a light-proof dialysis in a medium for 48-72 h, and obtaining the nano-micelle after performing a freeze-drying.

Preferably, the medium is replaced every 4 to 8 h during a process of the light-proof dialysis, and the medium is deionized water having a pH of 8 to 10 corrected with triethylamine.

Preferably, the tetravalent platinum compound-bicyclic double-bond-containing amphiphilic polymer prodrug has the following structure:

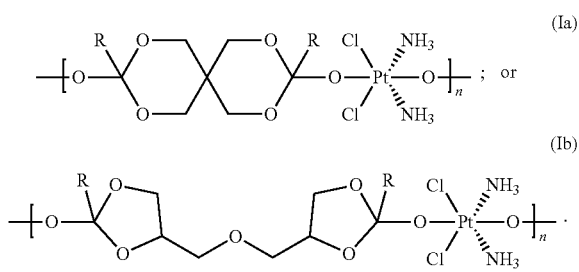

In the formula (Ia), R represents —$CH_3$ or —$CH_2CH_3$, and n is from 10 to 80. When R is —$CH_3$, the prepared nano-micelle is CPJ; and when R is —$CH_2CH_3$, the prepared nano-micelle is CCPJ.

In the formula (Ib), R represents —$CH_3$ or —$CH_2CH_3$, and n is from 10 to 80. When R is —$CH_3$, the prepared nano-micelle is FCPJ; and when R is —$CH_2CH_3$, the prepared nano-micelle is FCCPJ.

In a further aspect, an application of the above-mentioned nano-micelle as a drug carrier for preparing a novel anti-tumor nano-pharmaceutical preparation is provided.

Preferably, the application is implemented by the following steps: dissolving the nano-micelle in dimethyl sulfoxide, and adding a cargo to obtain a solution; after being fully dissolved, placing the solution in a dialysis bag with a molecular weight cutoff value of 3500 for performing a light-proof dialysis in a medium for 48-72 h, and obtaining the novel anti-tumor nano-pharmaceutical preparation after performing a freeze-drying. During the dialysis process, due to the amphiphilic property of the polymer, the cargo with a hydrophobic property is encapsulated into an inner core of the nano-micelle to form the novel anti-tumor nano-pharmaceutical preparation.

Preferably, the cargo is one or more selected from the group consisting of an anti-tumor drug, an immune factor, a photosensitizer, and an interference factor. The anti-tumor drug is one or more selected from the group consisting of camptothecin, paclitaxel, docetaxel, doxorubicin, 5-fluorouracil, etoposide, and bleomycin. The immune factor is one or more selected from the group consisting of whey protein, lysozyme, and proline-rich polypeptide. The photosensitizer is one or more selected from the group consisting of hematoporphyrin derivative, 5-aminolevulinic acid, and m-tetrahydroxyphenyl chlorin. The interference factor is one or more selected from the group consisting of IFN-α1 type, IFN-α2 type, Roferon-A, Wellferon and combined interferon. The medium is replaced every 4 to 8 h during the process of light-proof dialysis, and the medium is deionized water having a pH of 8 to 10 corrected with triethylamine.

Compared with the prior art, advantages of the present invention are as follows. The amphiphilic polymer prodrug of the present invention contains a high concentration of tetravalent platinum, and the potential of the tetravalent platinum is regulated to a suitable value which can prolong the half-life of the drug, so that the prodrug can stably exist in the blood for a long time. On the basis of high content of tetravalent platinum, the chloride ion of the tetravalent platinum compound can provide desired targeting ability for the micelles to enter the tumor cells, so that the drug can be efficiently accumulated in the tumor site. On the basis of reducible tetravalent platinum, the pH-sensitive ortho ester bond is introduced, making the drug more sensitive to the environment, which results in a faster drug release and a better therapeutic effect. In addition, the nano-micelle prepared by the amphiphilic polymer prodrug of the present invention can embed one or more anti-tumor reagents to prepare a novel anti-tumor nano-pharmaceutical preparation. By intravenous administration of the novel anti-tumor nano-pharmaceutical preparation, a better tumor treatment effect and an effect of completely curing the solid tumor are achieved (the cure rate reaches 80%). The preparation method of the present invention is relatively simple, economical and easy to operate.

DETAILED DESCRIPTION OF THE EMBODIMENTS

Figure 1A:
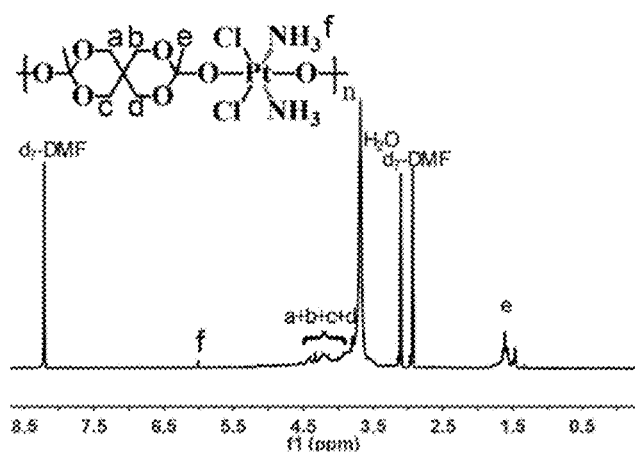
FIG. 1A is a $^1$H NMR spectrum of a nano-micelle CPJ prepared in Embodiment 3.

The embodiments of the present invention will be described in detail below. The embodiments are implemented on the premise of the technical solutions of the present invention; and detailed implementation manners and specific operation procedures are provided. However, the protective scope of the present invention is not limited to the following embodiments.

Embodiment 1

The specific steps of preparing an axially dihydroxy-coordinated tetravalent platinum compound (oxoplatin) are as follows. 200 mg of divalent cisplatin (CDDP), 6 mL of deionized water and 6.5 mL of 30% hydrogen peroxide were added to a 50 mL reaction bottle. The reaction was carried out at 65° C.-75° C. (preferably 70° C.) for 10-12 h under a light-proof condition, and after concentration by rotary evaporation, cooling with ice water and suction filtering were performed to obtain a reaction product. The reaction product was washed successively with ice water, ethanol and diethyl ether, and subjected to vacuum drying to obtain the axially dihydroxy-coordinated tetravalent platinum compound Pt(IV)-(OH)$_2$ (oxoplatin).

Embodiment 2

(1) Preparation of Six-Membered Ring- and Double-Bond-Containing Orthoester Precursor.

DMTU: 8.5 g (76 mmol) of potassium tert-butoxide and 70 mL of tert-butanol were added to a three-necked flask equipped with a reflux condenser and a magnetic stir bar; and the three-necked flask was filled with nitrogen gas for protection. After solid in the three-necked flask was disappeared at room temperature, 3,9-dibromomethyl-2,4,8,10-tetraoxaspiro[5.5]undecane (BBTU) (12 g, 35 mmol) was added to obtain a mixture, and the mixture reacted at a reflux temperature for 12 h. The tert-butanol was distilled off under normal pressure, and then the tert-butanol was removed completely by distillation under reduced pressure. 60 mL of anhydrous petroleum ether was added and stirred at the reflux temperature, and the temperature was reduced to 40° C. after 1 h. Then, a suction filtering was performed to remove the solid; and the liquid was placed in a freezer for freezing overnight, and then recrystallized twice with petroleum ether. Finally, a white product, i.e., 3,9-dimethylene-2,4,8,10-tetraoxaspiro[5.5]undecane (DMTU), was obtained in a yield of 83%.

DETOSU: A 200 mL photochemical reactor with a thermowell and a condenser, which was filled with nitrogen gas for protection, was taken. 100 mL of n-pentane and 20.72 g (97.6 mmol) of 3,9-divinyl-2,4,8,10-tetraoxaspiro-undecane were added to the reactor; and the gas in the solvent was removed by stirring at the reflux temperature for 40 min. Then 0.059 mL (87.9 mg) of iron pentacarbonyl was added to the mixture and the stirring was continued for 15 min at the reflux temperature. The reaction solution was irradiated with 450 W medium-pressure quartz pump vapor arc lamp reflector for 30 min at the reflux temperature, then the reflector was removed, and the reaction was continued at the reflux temperature for 90 min. Then the reaction was performed under light for 40 min, the reflector was removed, and the reaction was continued for 6 h. When the raw materials were shown to have been consumed and the isomer materials were less than 5%, the reaction solution was cooled and stirred overnight. Finally, 0.5 mL of triethylamine was added, n-pentane was removed by distillation, and 3,9-diethylene-2,4,8,10-tetraoxaspiro-undecane (DETOSU) crude product was obtained by vacuum drying. The crude product was then dissolved in n-heptane and distilled three times to obtain pure DETOSU.

(2) Preparation of Five-Membered Ring- and Double-Bond-Containing Orthoester Precursor.

OMMD: 1) digylcerol (33.2 g, 0.2 mol), dibromo-1,1-dimethoxyethane (76.4 g, 0.454 mol), p-toluenesulfonic acid (p-TSA, 0.36 g, 2.11 mmol) and 80 mL of diglyme were added to a three-necked flask equipped with a Claisen distillation head and a magnetic stir bar. After heating to 110° C. for reaction for 3 h, the temperature was raised to 150° C. and kept for 2 h, then a large amount of methanol, etc. were removed. The temperature was lowered to 110° C., and the remaining methanol and diglyme were distilled off under reduced pressure. The remaining reactants were gradually added dropwise to ice water with violent stirring at 110° C. to obtain a solution. Then, suction filtering and washing with ice water were performed. Finally, recrystallization was performed with acetone twice to obtain 4,4-dimethoxy-bis-(2-bromomethyl-1,3-dioxolane) (OMBD) in a yield of 85.2%. 2) The OMMD was prepared by the preparation method of the above DMTU, but the difference was that the BBTU was replaced by the OMBD, and the yield was 80%.

EEDMMD: 1) diglycerol (11.25 g, 0.068 mol), 3,3-diethoxypropene (20.0 g, 0.154 mol), p-toluenesulfonic acid (p-TSA, 0.12 g, 0.72 mmol) and 100 mL of toluene or benzene were added to a three-necked flask with a condensing reflux water segregator under nitrogen gas protection; heating was performed to the boiling point of the solvent; and stirring was performed for 5-8 h. After the solvent was removed, 4,4-dimethoxy-bis-(2-vinyl-1,3-dioxolane) (OMVD) was obtained by a gel column chromatography with ethyl acetate and n-hexane having a volume ratio of 5-20:1, and the yield was 81.3%. 2) The EEDMMD was prepared by the preparation method of the above DETOSU, but the difference was that the 3,9-divinyl-2,4,8,10-tetraoxaspiro-undecane was replaced by the OMVD, and the yield was 80%.

Embodiment 3

(1) Preparation of amphiphilic polymer prodrug: 50 mg (0.27 mmol) of the 3,9-dimethylene-2,4,8,10-tetraoxaspiro [5.5]undecane (DMTU) prepared in Embodiment 2 and 90.7 mg (0.27 mmol) of the axially dihydroxy-coordinated tetravalent platinum compound (oxoplatin) prepared in Embodiment 1 were added to a 100 mL reaction flask. 9.2 mg of p-toluenesulfonamide (p-TSA) was dissolved in 100 mL of anhydrous dimethyl sulfoxide (DMSO) to obtain p-toluenesulfonamide dimethyl sulfoxide solution. Then, 1 mL of the p-toluenesulfonamide dimethyl sulfoxide solution was added to the reaction flask, 5-10 mL of anhydrous DMSO was finally added, and reaction was performed with stirring at 60° C. for 24 h under protection of a nitrogen atmosphere. After the reaction was completed, 2 to 3 drops of triethylamine were added to terminate the reaction, and the amphiphilic polymer prodrug was obtained.

(2) Preparation of nano-micelle CPJ: the amphiphilic polymer prodrug prepared in the step (1) was transferred to a dialysis bag with a molecular weight cutoff value of 3500 in deionized water with a pH of 8 corrected by triethylamine to carry out a light-proof dialysis for 48-72 h. During the light-proof dialysis, the deionized water with a corrected pH of 8 was replaced every 4 to 8 h. After freeze-drying, white powdery nano-micelle CPJ was obtained. During the dialysis process, due to the amphiphilic property of the polymer, nano-micelle particles were gradually formed.

Figure 1B:
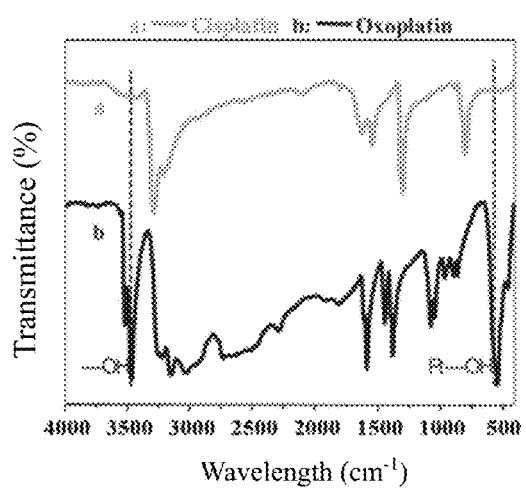
FIGS. 1B and 1C are FT-IR spectra of related materials for preparing the nano-micelle CPJ and the CPJ in Embodiment 3.
Figure 1C:
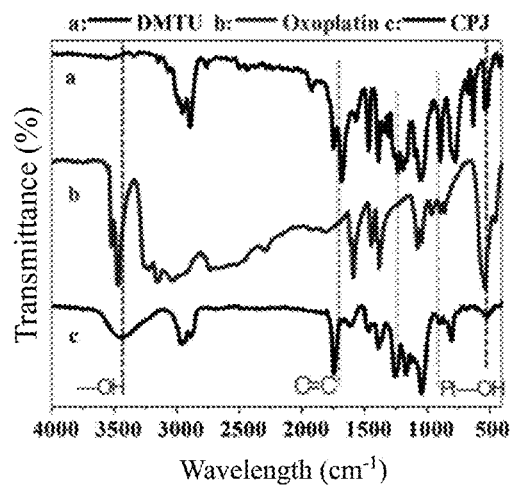

The prodrug nano-micelle CPJ was detected by a nuclear magnetic resonance spectrometer and a Fourier transform infrared spectroscopic analyzer. The detection conditions were as follows: the sample was mixed and ground uniformly with KBr at room temperature, and scanned at a speed of 2 mm/s in the range of 500-4000 $cm^{-1}$. The results were shown in FIGS. 1A-1C, wherein FIG. 1A is a $^1$H NMR spectrum of CPJ. It can be concluded from FIG. 1A that the proton peaks corresponding to the prepared nano-micelle CPJ have corresponding attribution on the $^1$H NMR, indicating that the structure of CPJ is correct. FIGS. 1B and 1C are FT-IR spectra of related materials for preparing nano-micelle CPJ and CPJ. It can be seen from FIGS. 1B and 1C that the tetravalent platinum compound exhibits a stretching vibration peak of the hydroxyl groups at two ends along the axial direction at the corresponding position, and after the reaction, the stretching vibrational peak of the hydroxyl groups at two ends along the axial direction almost disappears, and the stretching vibrational peak of the double-bond of the six-membered ring- and double-bond-containing monomer also gradually disappeared with its consumption, further indicating that the correctness of the structure of CPJ.

Embodiment 4

(1) Preparation of amphiphilic polymer prodrug: 80 mg (0.38 mmol) of the 3,9-diethylene-2,4,8,10-tetraoxaspiro [5.5]undecane (DETOSU) prepared in Embodiment 2 and 126.9 mg (0.38 mmol) of the oxoplatin prepared in Embodiment 1 were added to a 100 mL reaction flask. 13.0 mg of p-toluenesulfonamide (p-TSA) was dissolved in anhydrous dimethyl sulfoxide (DMSO) to obtain a p-toluenesulfonamide dimethyl sulfoxide solution. Then, 1 mL of the p-toluenesulfonamide dimethyl sulfoxide solution was added to the reaction flask, 6-12 mL of anhydrous DMSO was finally added, and reaction was performed with stirring at 50° C. for 72 h under protection of a nitrogen atmosphere. After the reaction was completed, 2 to 3 drops of triethylamine were added to terminate the reaction, and the amphiphilic polymer prodrug was obtained.

(2) Preparation of nano-micelle CCPJ: the amphiphilic polymer prodrug prepared in the step (1) was transferred to a dialysis bag with a molecular weight cutoff value of 3500 in deionized water with a pH of 9 corrected by triethylamine to carry out a light-proof dialysis for 48-72 h. During the light-proof dialysis, the deionized water with a corrected pH of 9 was replaced every 4 to 8 h. After freeze-drying, white powdery nano-micelle CCPJ was obtained.

Embodiment 5

(1) Preparation of amphiphilic polymer prodrug: 100 mg (0.64 mmol) of the 4,4-dimethoxy-bis-(2-methyl-1,3-dioxolane) (OMMD) prepared in Embodiment 2 and 213.9 mg (0.64 mmol) of the oxoplatin prepared in Embodiment 1 were added to a 100 mL reaction flask. 21.9 mg of p-toluenesulfonamide (p-TSA) was dissolved in anhydrous dimethyl sulfoxide (DMSO) to obtain a p-toluenesulfonamide dimethyl sulfoxide solution. Then, 1 mL of the p-toluenesulfonamide dimethyl sulfoxide solution was added to the reaction flask, 10-15 mL of anhydrous DMSO was finally added, and reaction was performed with stirring at 55° C. for 48 h under protection of a nitrogen atmosphere. After the reaction was completed, 2 to 3 drops of triethylamine were added to terminate the reaction, and the amphiphilic polymer prodrug was obtained.

(2) Preparation of nano-micelle FCPJ: the amphiphilic polymer prodrug prepared in the step (1) was transferred to a dialysis bag with a molecular weight cutoff value of 3500 in deionized water with a pH of 10 corrected by triethylamine to carry out a light-proof dialysis for 60 h. During the light-proof dialysis, the deionized water with a corrected pH of 10 was replaced every 4 to 8 h. After freeze-drying, white powdery nano-micelle FCPJ was obtained.

Embodiment 6

(1) Preparation of amphiphilic polymer prodrug: 100 mg (0.54 mmol) of the (Z)-2-ethylidene-4-[(E)-2-ethylidene-1,3-dioxolan-4-yl-methoxy-methyl]-1,3-dioxolane (EE-DMMD) prepared in Embodiment 2 and 181.3 mg (0.54 mmol) of the oxoplatin prepared in Embodiment 1 were added to a 100 mL reaction flask. 18.5 mg of p-toluenesulfonamide (p-TSA) was dissolved in anhydrous dimethyl sulfoxide (DMSO) to obtain a p-toluenesulfonamide dimethyl sulfoxide solution. Then, 1 mL of the p-toluenesulfonamide dimethyl sulfoxide solution was added to the reaction flask, 5-10 mL of anhydrous DMSO was finally added, and reaction was performed with stirring at 53° C. for 52 h under protection of a nitrogen atmosphere. After the reaction was completed, 2 to 3 drops of triethylamine were added to terminate the reaction, and the amphiphilic polymer prodrug was obtained.

(2) Preparation of nano-micelle FFCPJ: the amphiphilic polymer prodrug prepared in the step (1) was transferred to a dialysis bag with a molecular weight cutoff value of 3500 in deionized water with a pH of 9.5 corrected by triethylamine to carry out a light-proof dialysis for 52 h. During the light-proof dialysis, the deionized water with a corrected pH of 9.5 was replaced every 4 to 8 h. After freeze-drying, white powdery nano-micelle FFCPJ was obtained.

Embodiment 7

Preparations of novel anti-tumor nano-pharmaceutical preparations (doxorubicin-loaded prodrug micelles, CPJ/DOX, CCPJ/DOX, FCPJ/DOX and FCCPJ/DOX): 20 mg of the nano-micelles CPJ, CCPJ, FCPJ and FCCPJ prepared in Embodiments 3-6 were weighed separately, and then separately added in 0.4 mL of anhydrous DMSO for sufficient dissolution; subsequently, 4 mg of doxorubicin was further added to dissolve therein to obtain a solution, respectively. Each solution was transferred to a dialysis bag with a molecular weight cutoff value of 3500 in deionized water with a pH of 9 corrected by triethylamine to carry out a light-proof dialysis for 52 h. During the light-proof dialysis, the deionized water with a corrected pH of 9 was replaced every 4 h. After freeze-drying, novel anti-tumor nano-pharmaceutical preparations (doxorubicin-loaded prodrug micelles, CPJ/DOX, CCPJ/DOX, FCPJ/DOX and FCCPJ/DOX) were obtained.

The drug loading capacity and drug loading efficiency of the doxorubicin-loaded prodrug micelles were measured by a microplate reader with a wavelength of 481 nm. The results are shown in Table 1, and the calculation formula is as follows.

Drug loading capacity (DLC %)=the amount of doxorubicin in drug-loaded micelles/the total amount of drug-loaded nano-micelles×100%; and drug loading efficiency (DLE %)=the amount of doxorubicin in the drug-loaded micelles/the total adding amount of doxorubicin×100%.

The potentials (Zeta) of four doxorubicin-loaded prodrug micelles were measured by a dynamic light scattering instrument with a 6 mM laser, an incident light having a wavelength of 633 nm and a scattering angle of 173 degrees. The results are shown in Table 1.

TABLE 1

Drug loading capacity, drug loading efficiency and potential of doxorubicin-loaded prodrug micelles

| Drug-loaded micelle | DLC$^a$ (%) | DLE$^a$ (%) | Zeta$^b$ (mV) |
|---|---|---|---|
| CPJ/DOX | 9.6 ± 1.9 | 79.5 ± 6.3 | 0.487 ± 0.11 |
| CCPJ/DOX | 10.3 ± 2.2 | 69.8 ± 4.8 | −0.287 ± 0.08 |
| FCPJ/DOX | 8.9 ± 1.5 | 74.7 ± 5.2 | 0.382 ± 0.103 |
| FCCPJ/DOX | 11.2 ± 2.0 | 70.6 ± 5.1 | −0.114 ± 0.092 |

Note:
$^a$represents that the value is measured by microplate reader; and
$^b$represents that the value is measured by dynamic light scattering instrument.

As can be concluded from Table 1, the four polymer prodrug micelles prepared above can effectively load the drug doxorubicin; and the potentials are close to neutral, which is suitable for maintaining stable characteristics in the blood circulation.

Embodiment 8

Determination of the molecular weights and molecular weight distributions, and calculation of yield of the nano-micelles CPJ, CCPJ, FCPJ and FCCPJ prepared in Embodiments 3-6. A certain amount of nano-micelles CPJ, CCPJ, FCPJ and FCCPJ were respectively weighed, and dissolved with chromatogram grade dimethylformamide (DMF) and the final concentration was guaranteed to be 2 mg/mL, and a filtration was carried out with an organic phase filter with an aperture of 0.45 m. The molecular weight (number average molecular weight Mn, weight average molecular weight Mw) and molecular weight distribution (polydispersity index PDI, ratio of Mw to Mn) were measured by Waters 1515 GPC, wherein DMF was used as the mobile phase, the flow rate was 1 mL/min, and the sample volume was 60 μL. The yields of the obtained nano-micelles can be calculated according to the molecular weight measured by the above method. The results are shown in Table 2 below.

The potentials (Zeta) of nano-micelles CPJ, CCPJ, FCPJ and FCCPJ with a concentration of 1 mg/mL prepared in Embodiments 3-6 were measured by a dynamic light scattering instrument with a 6 mM laser, an incident light having a wavelength of 633 nm and a scattering angle of 173 degrees. The results are shown in Table 2 below.

TABLE 2

Yield, molecular weight, molecular weight distribution and potential of nano-micelles prepared in Embodiments 3-6

| Nano-micelles | Yield | Mn$^a$ (×10$^4$) | Mw$^a$ (×10$^4$) | PDI$^a$ | Zeta$^b$ (mV) |
|---|---|---|---|---|---|
| CPJ | 52% | 0.7871 | 1.1408 | 1.45 | −35.3 |
| CCPJ | 60.2% | 1.653 | 2.41 | 1.46 | −21.3 |
| FCPJ | 67.5% | 2.907 | 3.815 | 1.31 | −41.8 |
| FCCPJ | 72.3% | 3.758 | 5.125 | 1.36 | −30.2 |

$^a$represents that the value is measured by gel permeation chromatography (GPC) with dimethylformamide (DMF) phase;
$^b$represents that the value is measured by dynamic light scattering instrument.

As can be concluded from Table 2, the yield of each of the four nano-micelles increase with the increase of the molecular weight, indicating that the reactivity of each of the four nano-micelles is increased, and the molecular weight distribution of each of the four nano-micelles is relatively uniform; the potentials of the four nano-micelles are all negative, probably due to the high negative charge of cisplatin, which also increases the stability of the drugs in the blood circulation.

Embodiment 9

Figure 2A:
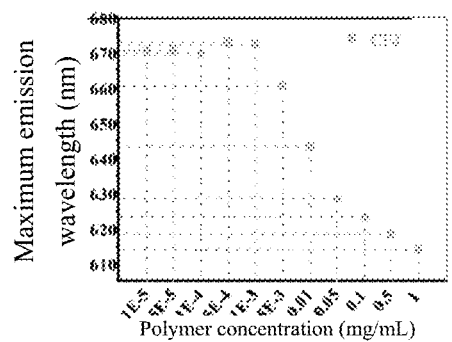
FIG. 2A shows a critical micelle curve of a nano-micelle CPJ in Embodiment 9.
Figure 2B:
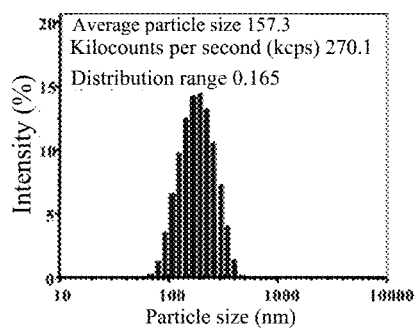
FIGS. 2B and 2C are diagrams showing average particle size distributions of the nano-micelle CPJ and a drug-loaded micelle CPJ/DOX in Embodiment 9, respectively.
Figure 2C:
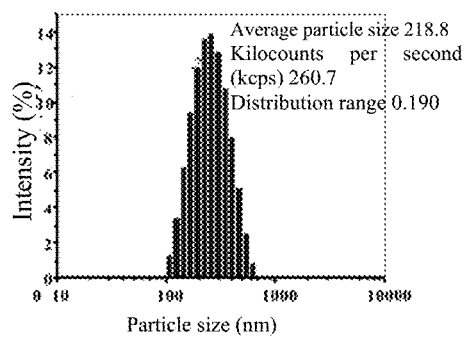
Figure 2D:
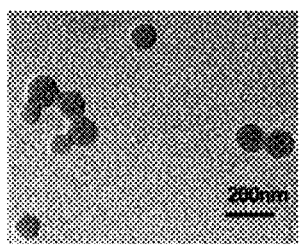
FIGS. 2D-2G are transmission electron micrographs of nano-micelles of CPJ, CCPJ, FCPJ and FCCPJ in Embodiment 9, respectively.
Figure 2E:
Figure 2F:
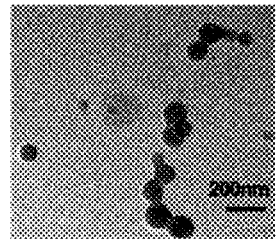
Figure 2G:
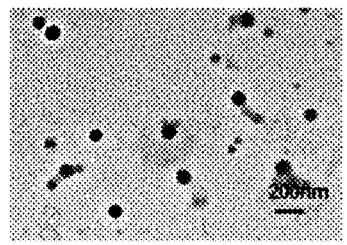

The critical micelle concentration of the nano-micelle CPJ prepared in Embodiment 3 was measured by a Nile Red detection method, and the critical micelle curve is shown in FIG. 2A. The particle size distributions of the nano-micelle CPJ prepared in Embodiment 3 and the drug-loaded micelle CPJ/DOX prepared in Embodiment 7 were detected by dynamic light scattering (DLS), and the results are shown in FIGS. 2B and 2C. The morphologies of the nano-micelles CPJ, CCPJ, FCPJ and FCCPJ prepared in Embodiments 3-6 was detected by transmission electron microscopy, and the results are shown in FIGS. 2D, 2E, 2F, and 2G.

As can be concluded from FIGS. 2A-2G, the prepared nano-micelle CPJ has a critical micelle concentration of $2.7 \times 10^{-4}$ mg/mL, indicating that the prepared micelle particles are relatively stable and simple to prepare. The prodrug micelle particles and the drug-loaded prodrug micelle particles have a particle size ranging from 100 to 200 nm, which are suitable as a nano-drug carrier for drug delivery to treat tumors, and the particle size distributions are relatively uniform. It can be seen from the transmission electron micrographs that the morphologies of the prepared four micelle particles are respectively in a uniform and regular spherical shape.

Embodiment 10 pH degradation and reduction of nano-micelles. The nano-micelle CPJ prepared in Embodiment 3 was prepared into a phosphate-buffered saline (PBS) solution with a final concentration of 1 mg/mL and a pH of 5.0, and a dithiothreitol (DTT) solution having a concentration of 20 mM. After a co-treatment for 24 h, high performance liquid chromatography (HPLC) was performed to detect the peak-appearance time to determine the structure of the nano-micelle CPJ. The results are shown in FIGS. 3A and 3B.

Figure 3:
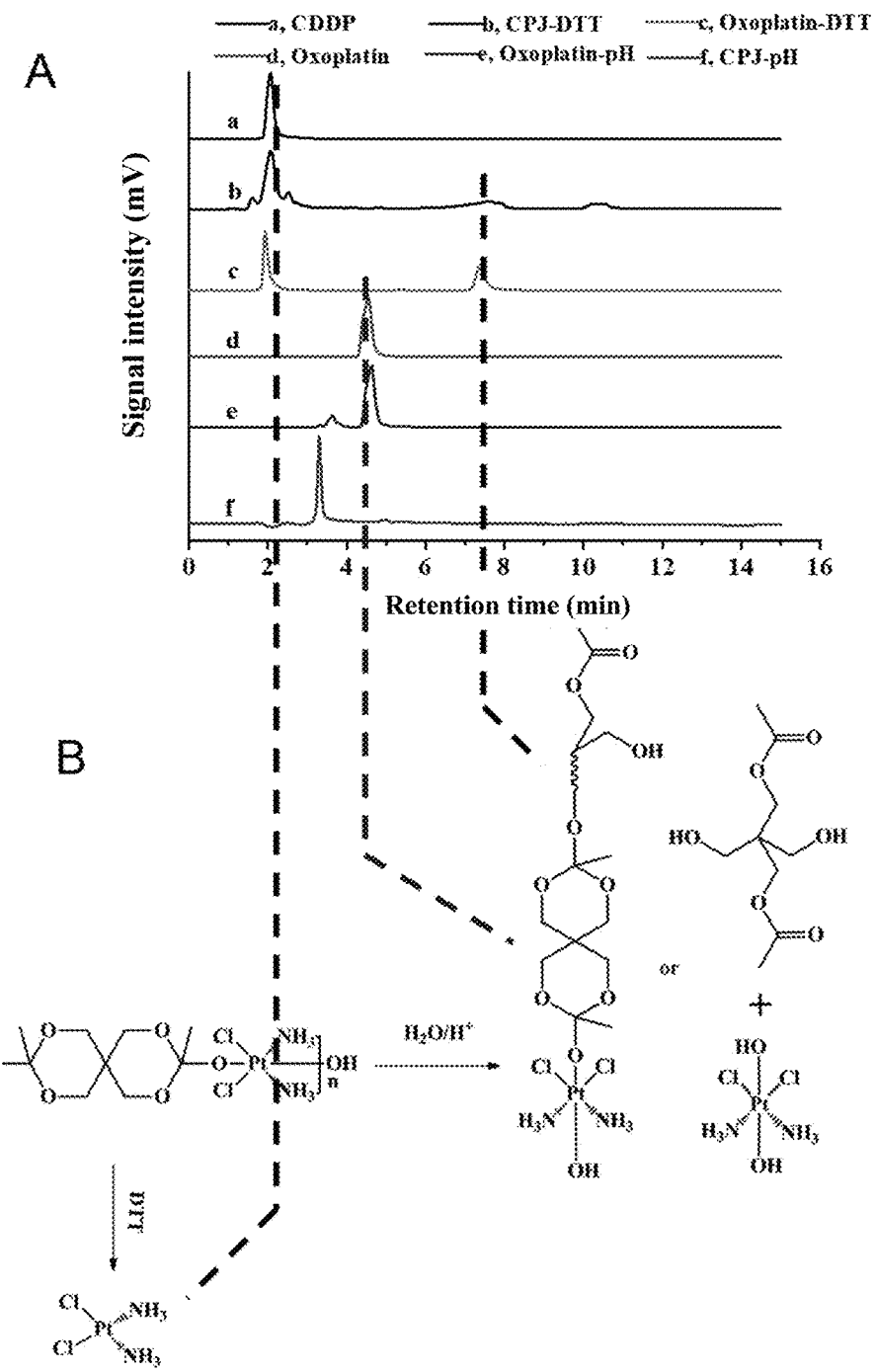
FIG. 3A is an HPLC chromatogram of a nano-micelle CPJ after subjected to an acid degradation or a reduction in Embodiment 10.
FIG. 3B is a diagram showing a degradation mechanism of the nano-micelle CPJ in Embodiment 10.
Figure 4A:
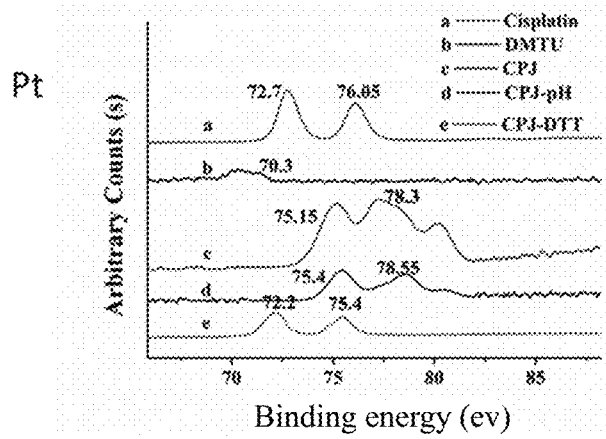
FIGS. 4A and 4B show X-ray photoelectron spectrum (XPS) curves of Pt after a degradation of a nano-micelle CPJ in Embodiment 11.
Figure 4B:
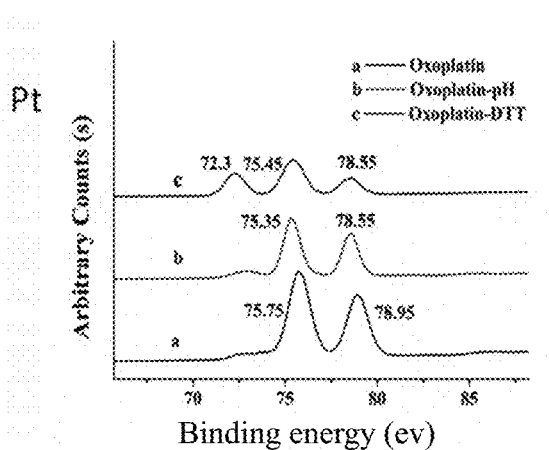
Figure 4C:
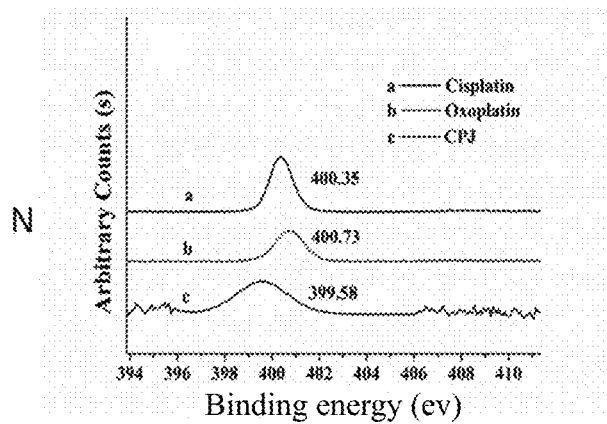
FIG. 4C shows X-ray photoelectron spectrum (XPS) curves of N after a degradation of a nano-micelle CPJ in Embodiment 11.
Figure 4D:
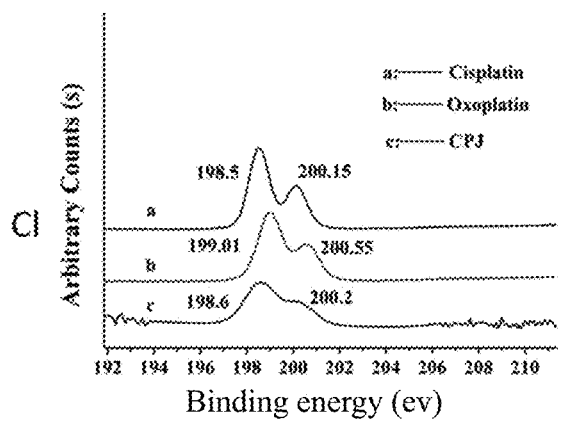
FIG. 4D shows X-ray photoelectron spectrum (XPS) curves of Cl after a degradation of a nano-micelle CPJ in Embodiment 11.

As can be seen from FIGS. 3A and 3B, after acid degradation or DTT reduction, due to the different products obtained, the peak-appearance time (position) of the products are different. As can be seen from the degradation mechanism diagram, the products of acid degradation still exists in the form of tetravalent platinum compounds, and because the products after acid degradation are complex, the peak-appearance time (position) of the products are different. However, the products, which are reduced to divalent cisplatin by DTT, have substantially the same peak-appearance time (position) as the original drug cisplatin, indicating that the polymer prodrug can be degraded and reduced to the original drug cisplatin under acidic or reductive conditions.

Embodiment 11

Determination of valence states of nano-micelles after pH degradation and reduction. The method of pH degradation and reduction was the same as that in Embodiment 10. After the nano-micelle CPJ was degraded and reduced, all the products were freeze-dried, and the valence states of Pt, N and Cl elements were detected by X-ray photoelectron spectroscopy (XPS). The results are shown in FIGS. 4A-4D. As can be seen from FIGS. 4A-4D, the products obtained by treatments of different pH still show a +4 valence, and the products show a +2 valence after reduction by DTT, which is the same as divalent cisplatin. Therefore, it can be proved that the above degradation mechanism is tenable; and it can be seen that the valence states of other elements are unchanged.

Embodiment 12

Figure 5A:
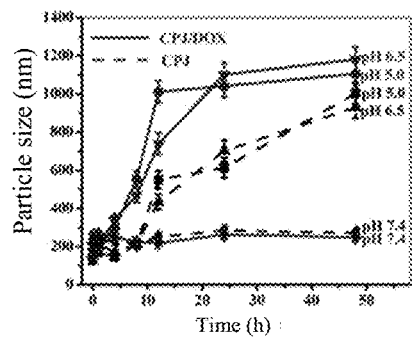
FIG. 5A is a diagram showing changes of particle sizes of a nano-micelle CPJ and a drug-loaded micelle CPJ/DOX after subjected to a pH degradation in Embodiment 12.
Figure 5B:
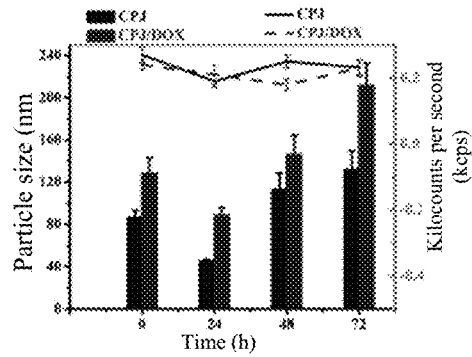
FIG. 5B is a diagram showing changes of particle sizes of the nano-micelle CPJ and the drug-loaded micelle CPJ/DOX in serum of Embodiment 12.
Figure 5C:
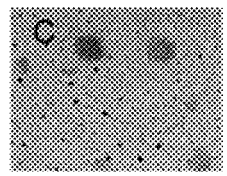
FIGS. 5C and 5D are transmission electron micrographs of the nano-micelle CPJ and the drug-loaded micelle CPJ/DOX after 72 h in serum of Embodiment 12.
Figure 5D:
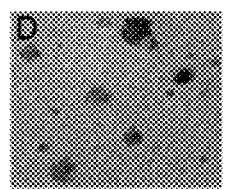
Figure 5E:
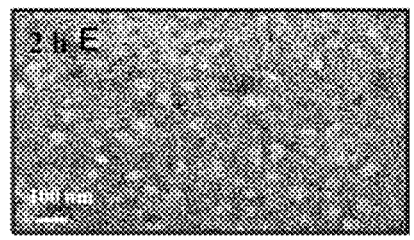
FIGS. 5E-5J are transmission electron micrographs of the nano-micelle CPJ and the drug-loaded micelle CPJ/DOX in the blood of mice after 2, 4, 8, 12, 24, and 48 h of Embodiment 12.
Figure 5F:
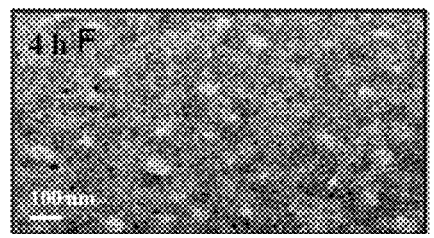
Figure 5G:
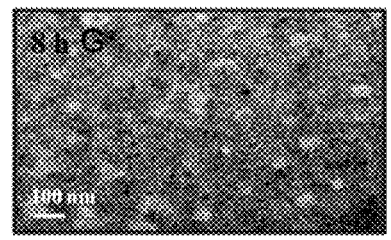
Figure 5H:
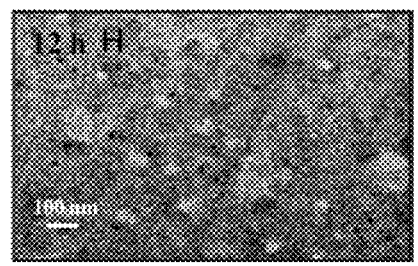
Figure 5I:
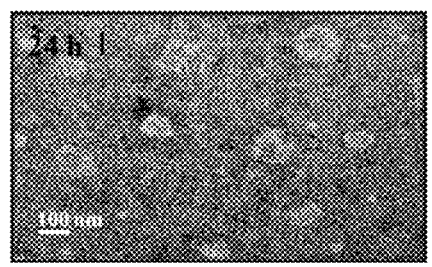
Figure 5J:
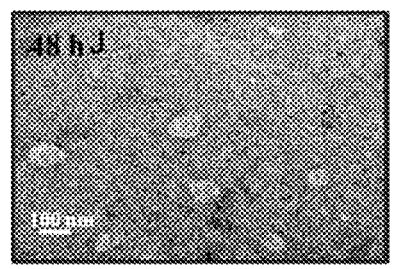

Determination of changes of particle sizes of CPJ and its drug-loaded micelles under different pH environments, detection of stability of CPJ and its drug-loaded micelles in serum, and stability test of drug-loaded micelles in blood circulation. The nano-micelle CPJ prepared in Embodiment 3 and the drug-loaded micelle CPJ/DOX prepared in Embodiment 7 were treated with PBS respectively having a pH of 5.0, 6.5 and 7.4 for different times, respectively; and the particle sizes of CPJ and CPJ/DOX were measured by dynamic light scattering (DLS) instrument over time, and the obtained results are shown in FIG. 5A. The nano-micelle CPJ prepared in Embodiment 3 and the drug-loaded micelle CPJ/DOX prepared in Embodiment 7 were treated with serum for different times, respectively, and the particle sizes of CPJ and CPJ/DOX were measured with time, and the obtained results are shown in FIG. 5B. The states of CPJ and CPJ/DOX were observed by transmission electron microscopy after treatment in serum for 72 h, and the results are shown in FIGS. 5C and 5D. The drug-loaded micelle CPJ/DOX was intravenously injected into a mouse at a therapeutic dose (the amount of Pt/the body weight of the mouse is 6 mg/kg), and the blood samples were taken at 2 h, 4 h, 8 h, 12 h, 24 h and 48 h for detection. The changes of micelle particles at different time points were then observed by transmission electron microscopy, and the results are as shown in FIGS. 5E-5J.

As can be seen from FIGS. 5A-5J, there is a significant difference when pH is 5.0, 6.5 and 7.4. The stronger the acidity is, the faster the degradation rate will be. Moreover, at a pH of 6.5, the degradation rate is also very fast, indicating that the micelle particles are hypersensitive to pH. While at a pH of 7.4, the micelle particles were stable in both buffer and serum, which was confirmed by subsequent transmission electron micrograph. After the blood circulation in the body, it can also be seen that the micelle particles can circulate for a long time in the blood.

Embodiment 13

Detection of in-vitro release amount of nano-micelles and drug-loaded micelles. The nano-micelle CPJ prepared in Embodiment 3 and the drug-loaded micelle CPJ/DOX prepared in Embodiment 7 were separately suspended in PBS having different pH to prepare a suspension, respectively. Then, 1 mL of the suspension was separately taken and placed in a dialysis bag with a molecular weight cut off value of 3500, and the dialysis bag was tied tightly with a cotton thread and placed in a 50 mL EP tube. Three of the 50 mL EP tubes were provided for each of the nano-micelle CPJ group and drug-loaded micelle CPJ/DOX group, 10 mL of a buffer having a pH of 5.0, 6.5, and 7.4 were separately added to the three EP tubes, and three repetitions were set. The EP tubes were shaken at 37° C. and 120 rpm. 10 mL of the used buffer in each EP tube was taken at a predetermined time point and an equal amount of fresh buffer was added. Then, the concentrations of doxorubicin in three groups of 200 μl of the used buffer were measured; the release amount of doxorubicin was then calculated. While the Pt content was measured by inductively coupled plasma mass spectrometry (ICP-MS) to calculate the release amount of the Pt element. In the reducing environment, the release amount detection method in the above pH environment was used, and the difference is that when the buffer was prepared, DTT solution was added to prepare 20 mM buffer having a pH of 5.0, 6.5, and 7.4, respectively, the dialysis bag having molecular weight cut off value of 8-14 kD was used, and the release amount of drugs in the drug-loaded micelle CPJ/DOX was calculated according to the detected amounts of Pt element and doxorubicin of the drug-loaded micelle CPJ/DOX. The results are shown in FIGS. 6A and 6B.

Figure 6A:
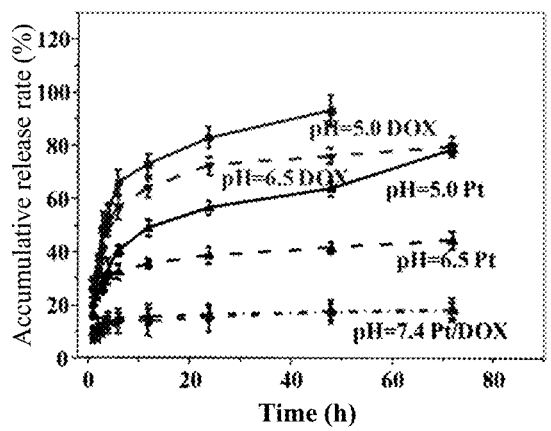
FIG. 6A is a diagram showing release curves of Pt from a nano-micelle CPJ and doxorubicin (DOX) from a drug-loaded micelle CPJ/DOX in different pH environments in Embodiment 13.
Figure 6B:
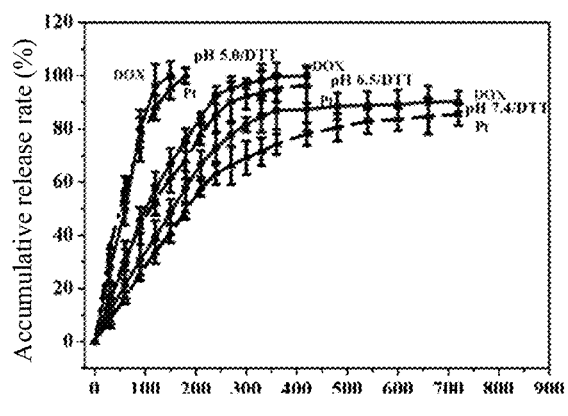
FIG. 6B is a diagram showing release curves of the Pt from the nano-micelle CPJ and the doxorubicin (DOX) from the drug-loaded micelle CPJ/DOX in different pH environments in the presence of DTT (Dithiothreitol) in Embodiment 13.

As can be seen from FIGS. 6A and 6B, under the independent pH condition, for the blank CPJ micelle particles, the release curves of Pt element were obtained according to the measured Pt content by ICP-MS; and for the drug-loaded micelle CPJ/DOX, the amount of doxorubicin was measured by a microplate reader to calculate the release amount of doxorubicin. While under the pH and reducing condition, the method for determining the drug release amount is the same as that described above, and it can be seen that in the presence of the reduction condition, the release rate is greatly increased as compared with that under the independent pH condition.

Embodiment 14

Cell culture: human breast cancer cells (MCF-7), human lung adenocarcinoma cells (A549) and human hepatoma cells (HepG2) were respectively added to a standard 6-well plate, and about $10^5$ cells are in each well. After overnight culture, the culture medium was removed, and 1.8 mL of fresh medium was added to prepare three cell culture solutions.

(1) Detection of Cellular Uptake of Nano-Micelles:

Drug: cisplatin (CDDP), tetravalent platinum compound (oxoplatin) prepared in Embodiment 1, nano-micelle CPJ prepared in Embodiment 3, and pH-degraded nano-micelle CPJ-pH in Embodiment 10.

Drug treatment: 0.2 mL of each of the above four drugs (the final concentration of Pt element was 2 μg/mL) was added to the three cell culture solutions, respectively, and the cells were cultured for 4 h and 8 h; subsequently, the culture medium was removed, and the cells were washed twice with PBS, and then treated with cell lysis buffer.

Figure 7A:
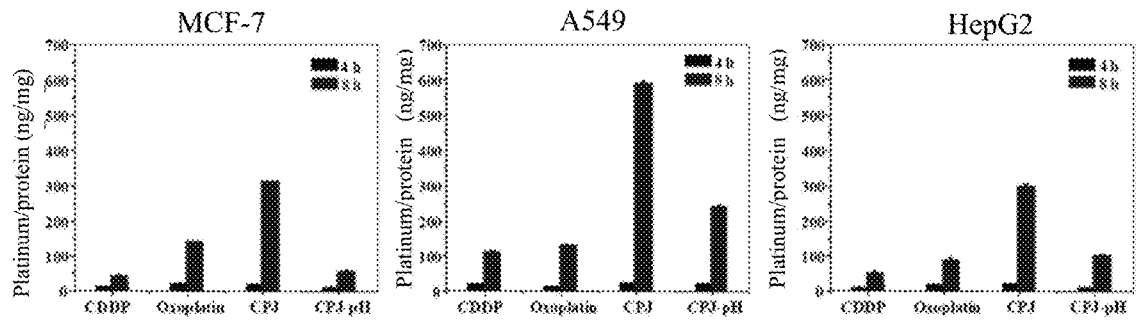
FIG. 7A is a diagram showing changes of Pt content of different drugs intaking in MCF-7, A549 and HepG2 cells over time in Embodiment 14.

Detection method: The content of Pt element was detected by ICP-MS, the protein content in the cells was detected by the BCA method, and the Pt content in a certain protein content was finally evaluated. The results are shown in FIG. 7A.

(2) Detection of Cellular Uptake of Drug-Loaded Micelles:

Drug: doxorubicin (DOX), and drug-loaded micelle CPJ/DOX prepared in Embodiment 7.

Drug treatment: 0.2 mL of each of the above two drugs (the final concentration of doxorubicin was 16 μg/mL) were added to the three cell culture solutions, respectively, and the cells were cultured for 4 h; subsequently, the culture medium was removed, and the cells were washed twice with PBS, fixed with 4% paraformaldehyde solution (about 5 min), and then washed twice with PBS; then, the nuclei of cells were stained with nuclear staining reagent (5 min), and the cells were washed twice with PBS.

Figure 7B:
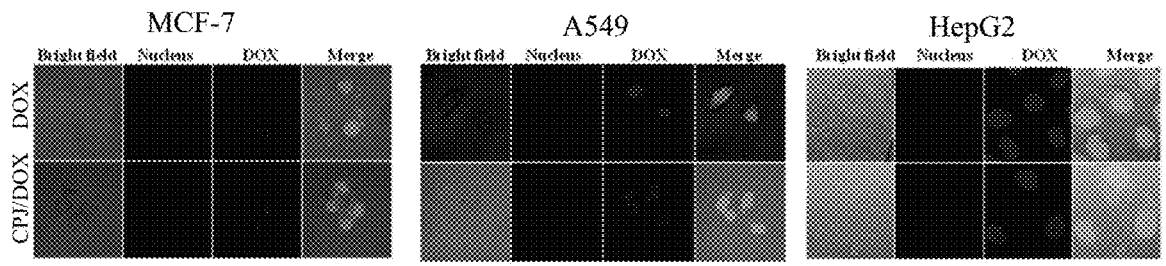
FIG. 7B shows confocal laser microscope images of MCF-7, A549 and HepG2 cells after uptake of different drugs in Embodiment 14.
Figure 7C:
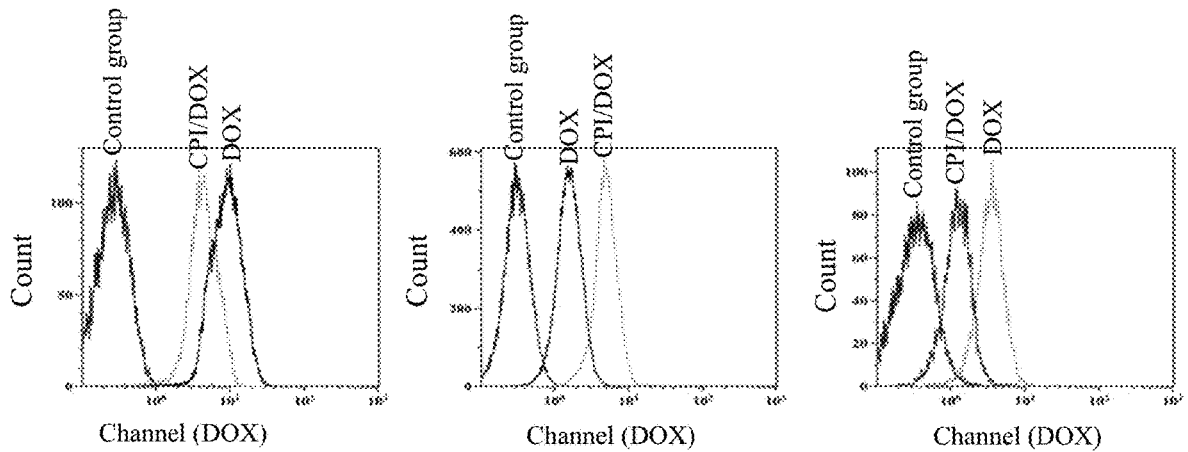
FIG. 7C shows diagrams of quantitative uptake of MCF-7, A549 and HepG2 cells after uptake of different drugs using a flow cytometer in Embodiment 14.
Figure 8A:
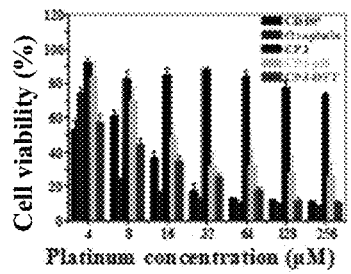
FIGS. 8A-8F are diagrams showing effects of different drugs on cell viabilities of MCF-7, A549 and HepG2 cells in Embodiment 15.
Figure 8B:
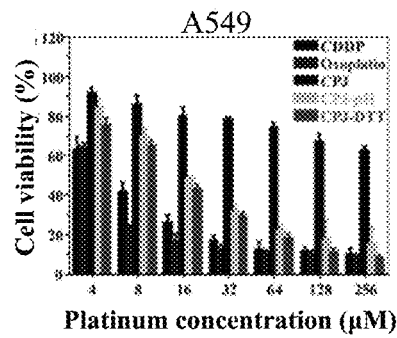
Figure 8C:
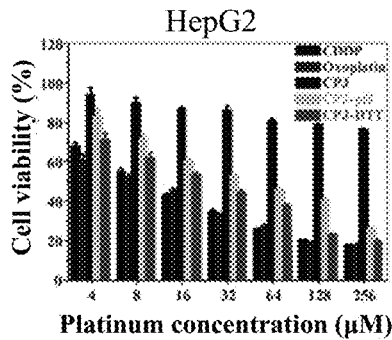
Figure 8D:
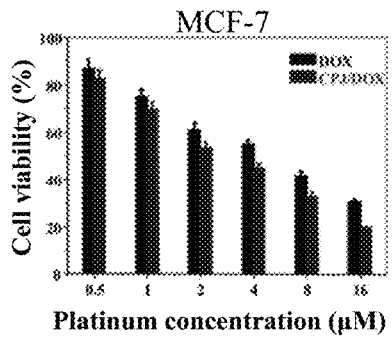
Figure 8E:
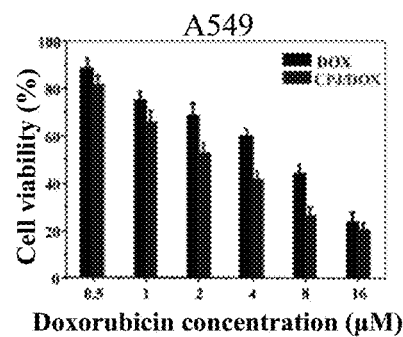
Figure 8F:
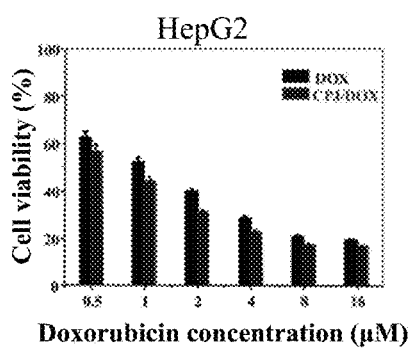

Detection method: The cellular uptake was qualitatively observed by confocal laser, as shown in FIG. 7B. It can be seen that cellular uptake can effectively occur in both the naked doxorubicin and the drug-loaded micelle particles. The quantitative measurement of uptake quantities of cells was carried out by flow cytometer, and the results are shown in FIG. 7C. As can be seen from FIG. 7C, the measured results are consistent with the above qualitative observed results shown in FIG. 7B. Moreover, it can be seen that A549 cells have a better uptake effect on drug-loaded micelle CPJ/DOX compared with naked doxorubicin.

Embodiment 15

Cytotoxicity Detection of Nano-Micelles and Drug-Loaded Micelles:

Cell culture: human breast cancer cells (MCF-7), human lung adenocarcinoma cells (A549) and human hepatoma cells (HepG2) were respectively added to a standard 6-well plate, and about 4000 cells are in each well. After 24 h of adherent culture, the culture medium was removed, and 180 l of fresh medium was added to prepare three cell culture solutions.

Drug: cisplatin (CDDP), tetravalent platinum compound (oxoplatin) prepared in Embodiment 1, nano-micelle CPJ prepared in Embodiment 3, pH-degraded nano-micelles CPJ-pH and CPJ-DTT in Embodiment 10, doxorubicin (DOX), and drug-loaded micelle CPJ/DOX prepared in Embodiment 7.

Drug treatment: 20 μL of each of the above first five drugs (Pt contents of the five drugs are the same) and 20 μL of each of the latter two drugs (doxorubicin contents of the two drugs are the same) were added to the three cell culture solutions, and the cells were cultured for 24 h. Then the culture medium was removed, and 180 μL of fresh medium and 20 μL of MTT (5 mg/mL) were added. After co-culture for 4 h, the culture medium was removed, 150 μL of DMSO was added, and shaken for 10 min. Thereafter, the cell culture solutions were taken and detected at a wavelength of 570 nm, and the corresponding OD values were measured by a microplate reader. The cell viability of each group was obtained based on comparison with the control group, and the results are shown in FIGS. 8A-8F. As can be seen from FIGS. 8A-8F, small molecule drugs, doxorubicin-loaded micelles and the products of degradation of polymer prodrugs have a good effect on killing cancer cells at a certain drug concentration. However, the killing of cancer cells by polymer prodrug micelles has a certain hysteresis caused by the process of ingestion, degradation and exertion.

Embodiment 16

Figure 9A:
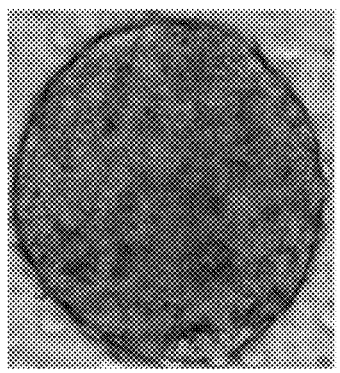
FIGS. 9A and 9B are diagrams of MCF-7 multicellular spheres using an inverted microscope in Embodiment 16.
Figure 9B:
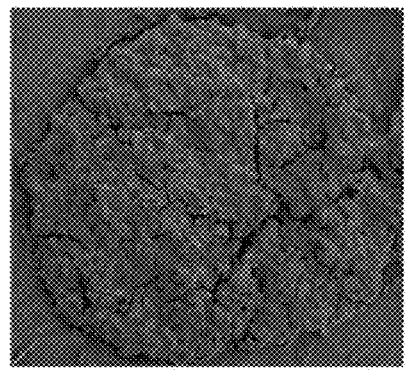
Figure 9C:
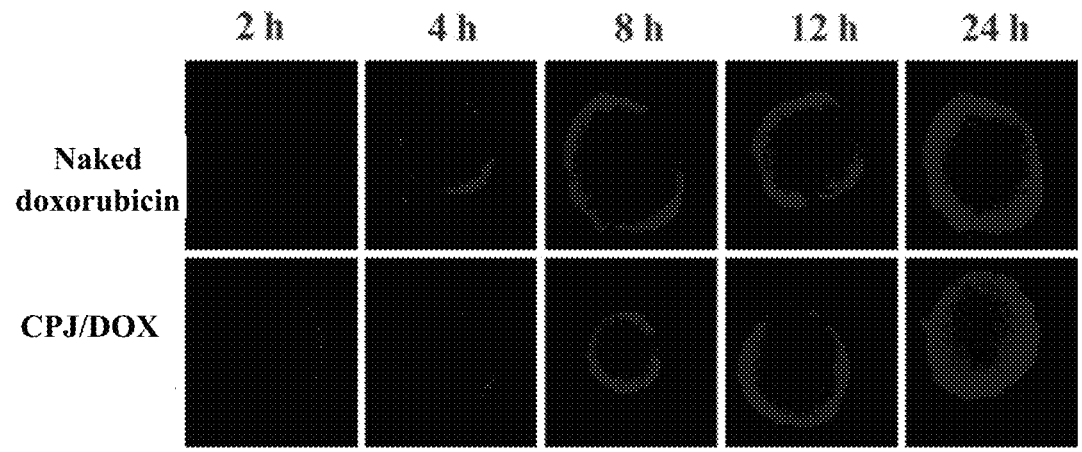
FIG. 9C is a confocal laser microscope image showing a permeability of doxorubicin in MCF-7 cells in Embodiment 16.

In-vitro simulation of 3D-permeation of drug-loaded micelles: human breast cancer cells (MCF-7) were cultured into multicellular spheres having a diameter of about 200-300 m, and observed with an inverted microscope and a scanning electron microscope, respectively. The results are shown in FIGS. 9A and 9B. 1.8 mL of culture medium containing multicellular spheres was randomly distributed into two 5 mL EP tubes, and approximately 8 to 10 multicellular spheres are in each EP tube. Then, 0.2 mL of doxorubicin (DOX) and drug-loaded micelle CPJ/DOX prepared in Embodiment 7 (the final concentration of doxorubicin was 16 μg/mL) were added to the two EP tubes. After co-culture for 2 h, 4 h, 8 h, 12 h and 24 h, the permeability of the DOX and CPJ/DOX were observed by confocal laser, and the results are shown in FIG. 9C. It can be seen from FIGS. 9A-9C that the culture of the cell mass is very successful, and the drug-loaded micelle particles can gradually permeate from the outer layer of the cell mass to the interior of the cell mass with the increase of time, so as to kill the cancer cells in the cell mass effectively.

Embodiment 17

Figure 10:
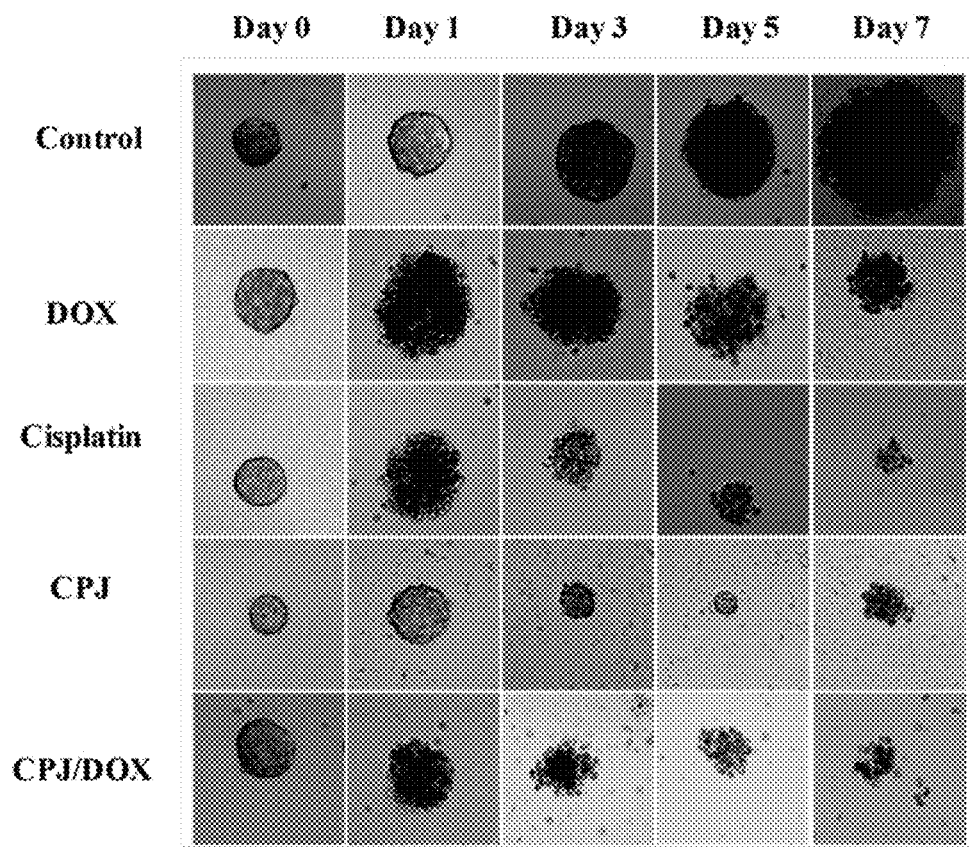
FIG. 10 is a micrograph showing inhibitory effects of different drugs on growths of MCF-7 multicellular spheres in Embodiment 17.

In-vitro simulation experiments of growth inhibition of multicellular 3-D spheres: breast cancer cell (MCF-7) multicellular spheres were cultured according to the method in Embodiment 16, which were co-cultured with different drugs (DOX, cisplatin, CPJ prepared in Embodiment 3 and CPJ/DOX prepared in Embodiment 7) in a 96-well plate for 0, 1, 3, 5, and 7 days; then the cell spheres were photographed by an inverted microscope to record the changes in the morphology and size of the cell spheres. The results are shown in FIG. 10. As can be seen from FIG. 10, the cell mass of the control group showed a growing trend with the extension of time, while the drug delivery group could well inhibit the growth of the cell mass and effectively kill the cancer cells. In addition, it can be clearly seen from FIG. 10 that the killing and inhibition effects achieved by particle group and drug-loaded particle group are both better than that achieved by the small molecule drug group.

Embodiment 18

Figure 11A:
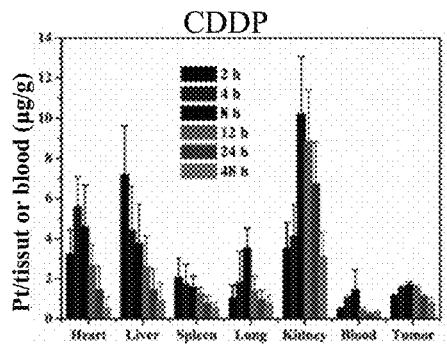
FIGS. 11A-11C are diagrams showing distributions of platinum of different drugs in mice in Embodiment 18.
Figure 11B:
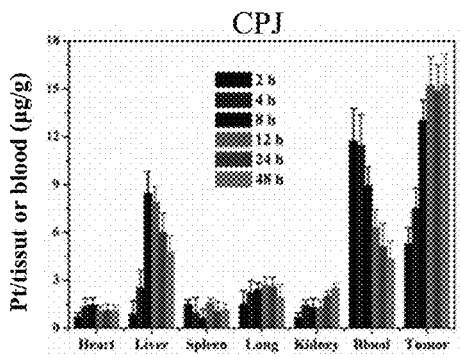
Figure 11C:
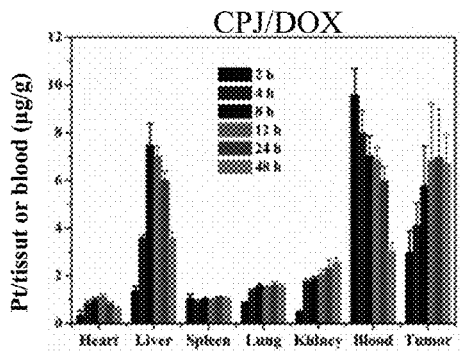
Figure 11D:
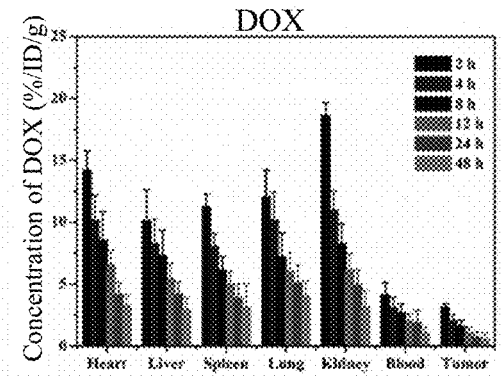
FIGS. 11D-11E are diagrams showing distributions of doxorubicin of different drugs in mice in Embodiment 18.
Figure 11E:
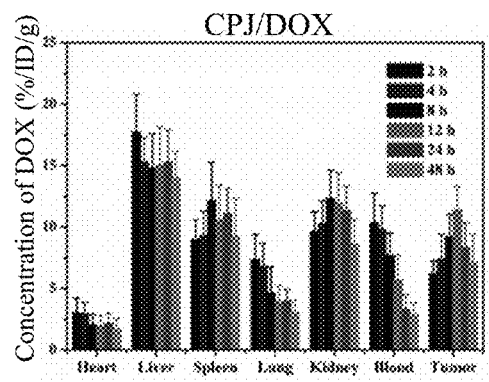

Detection of drug distribution: the cisplatin, the nano-micelle CPJ prepared in Embodiment 3 and the drug-loaded micelle CPJ/DOX prepared in Embodiment 7 were intravenously injected into different mice in an amount equal to a ratio of Pt content to mouse body weight of 6 mg/kg, respectively; the mice were then sacrificed at 2 h, 4 h, 8 h, 12 h, 24 h, and 48 h, respectively; subsequently, their organs and blood were taken, and the platinum distribution was measured by a microplate reader or ICP-MS. The results are shown in FIGS. 11A-11C. In addition, the doxorubicin and the drug-loaded micelle CPJ/DOX prepared in Embodiment 7 were intravenously injected into different mice in an amount equal to a ratio of doxorubicin content to mouse body weight of 6 mg/kg, respectively; the mice were then sacrificed at 2 h, 4 h, 8 h, 12 h, 24 h, and 48 h, respectively; subsequently, their organs and blood were taken, and the doxorubicin distribution was measured by a microplate reader or ICP-MS. The results are shown in FIGS. 11D-11E. As can be seen from FIGS. 11A-11C, small molecule drugs have a relatively high toxicity to the heart and other organs, and cannot circulate in the blood for a long time, so the small molecule drugs cannot be effectively accumulated in the tumor, and a good treatment effect cannot be achieved. However, the micelle particles and drug-loaded micelle particles can remain stable in the blood for a long time, and have a relatively small toxicity to the heart and other organs, thus capable of being effectively accumulated in the tumor site to achieve a good tumor treatment effect.

Embodiment 19

Figure 12A:
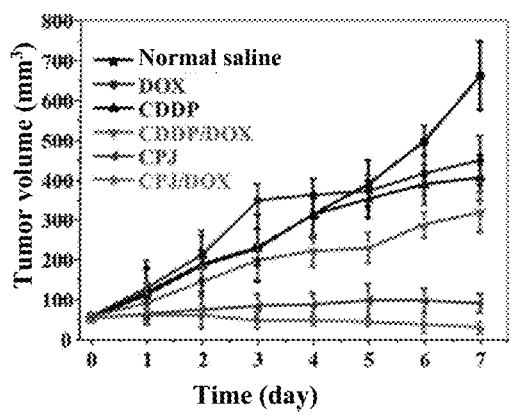
FIG. 12A shows changes in tumor volume of mice over time after a single administration in Embodiment 19.
Figure 12B:
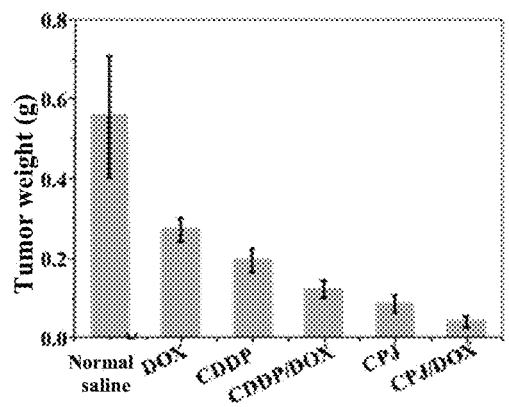
FIG. 12B shows changes in tumor mass of mice over time after a single administration in Embodiment 19.
Figure 12C:
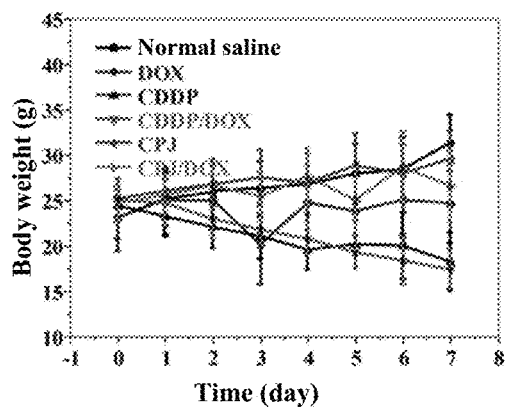
FIG. 12C shows changes in body weight of mice over time after a single administration in Embodiment 19.

Evaluation of the treatment effect of a single administration: according to the above-described method, different platinum compounds (including cisplatin, cisplatin/DOX and CPJ), free doxorubicin (6 mg/kg) and drug-loaded micelles (CPJ/DOX) prepared in Embodiment 7 were intravenously injected into mice (at an amount equal to a ratio of Pt content to mouse body weight of 6 mg/kg) for circulation and metabolize. The tumor volume, tumor mass and body weight of mice were then recorded at different time points, and the results are shown in FIGS. 12A-12C. As can be seen from FIGS. 12A-12C, the particle group and the drug-loaded particle group have less toxicity and side effects on mice, the body weight of the mice showed an increasing trend, and the particle group and the drug-loaded particle group have obvious inhibitory effect and even therapeutic effect on tumors; whereas the small molecule drugs have a certain inhibitory effect on tumors in mice, but their toxic side effects on mice are relatively high.

Embodiment 20

Figure 13A:
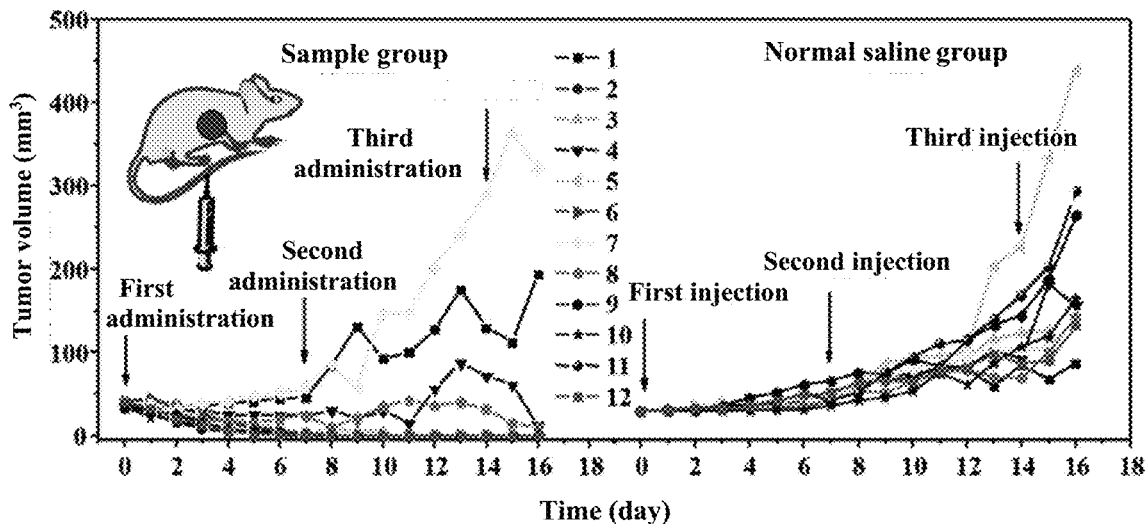
FIG. 13A shows changes in tumor volume of mice over time after multiple administrations in Embodiment 20.
Figure 13B:
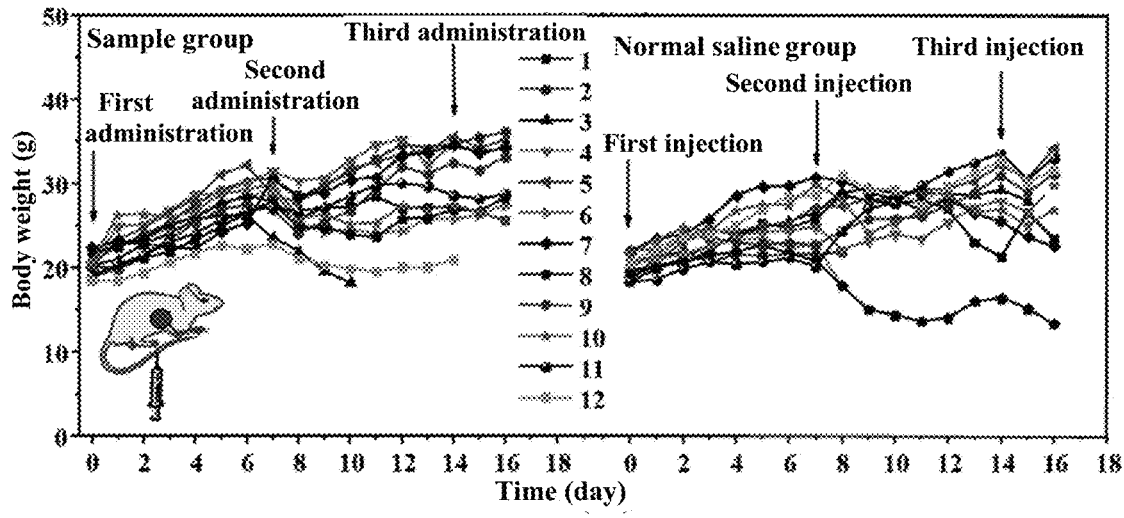
FIG. 13B shows changes in body weight of mice over time after multiple administrations in Embodiment 20.

Evaluation of the treatment effect of multiple administrations: on the basis of the evaluation of the first treatment effect, the drugs were further administered for multiple times, and then the treatment effect was evaluated. After the tumors of the mice grew to 40 mm³, 12 mice in each group were administered with the drugs every 7 days, and then the changes in tumor volume and body weight of the mice were recorded with the extension of time. In addition, a normal saline group was set as a parallel control group, and the results are shown in FIGS. 13A and 13B. As can be seen from FIGS. 13A and 13B, the changes in body weight and tumor size of the mice can be seen on $0^{th}$, $7^{th}$, and $14^{th}$ day administration groups and the normal saline control group, respectively. Moreover, in the drug administration groups, the tumors were very significantly inhibited and completely cured, and the body weight was gradually stabilized and increased with time; whereas, in the normal saline group, the tumor volume increased continuously, some mice died during this period, and the body weight tended to decrease after administration for a certain period of time.

The foregoing descriptions are merely preferred embodiments of the present invention, which are not used to limit the present invention. Any modifications, equivalent substitutions, improvements within the spirit and principle of the present invention should be included in the protective scope of the present invention.

What is claimed is:
1. A tetravalent platinum compound-bicyclic double-bond-containing amphiphilic polymer prodrug, comprising a structure as shown in formula (I):

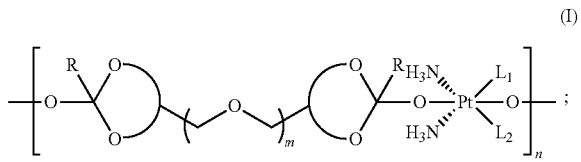

wherein, when m=1, the formula (I) is

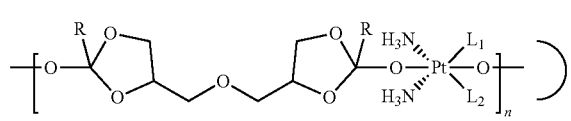

when m=0, the formula (I) is

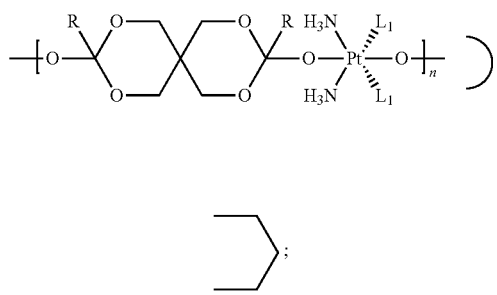

R is —CH$_3$ or —CH$_2$CH$_3$; L$_1$ is Cl, N$_3$, NO$_3$,

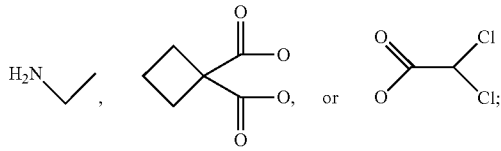

and L$_2$ is Cl, N$_3$, N$_3$,

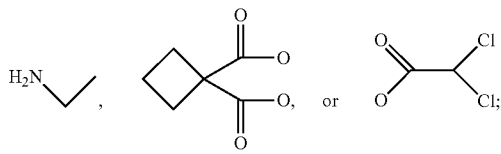

and n is from 10 to 80.

2. The tetravalent platinum compound-bicyclic double-bond-containing amphiphilic polymer prodrug according to claim 1, wherein L$_1$ is Cl, and L$_2$ is Cl.

3. A method of preparing the tetravalent platinum compound-bicyclic double-bond-containing amphiphilic polymer prodrug according to claim 1, wherein the method comprises the step of reacting an axially dihydroxy-coordinated tetravalent platinum compound as shown in formula (II) with a bicyclic double-bond-containing orthoester precursor as shown in formula (III);

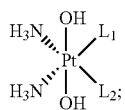 (II)

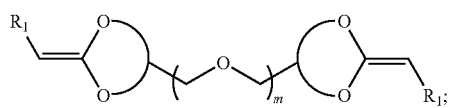 (III)

wherein
in the formula (II), L$_1$ is Cl, N$_3$, NO$_3$,

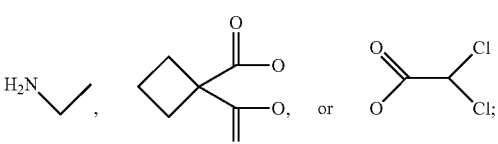

and L$_2$ is Cl, N$_3$, NO$_3$,

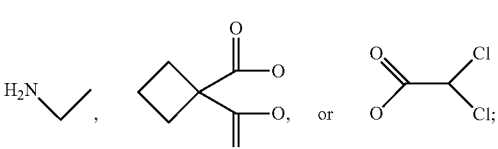

and
in the formula (III), when m=1, the formula (III) is

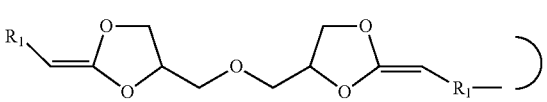

when m=0, the formula (III) is

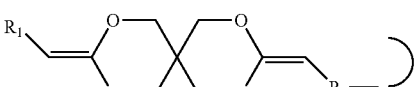

and R$_1$ is —H or —CH$_3$.

4. The method of preparing the tetravalent platinum compound-bicyclic double-bond-containing amphiphilic polymer prodrug according to claim 3, wherein the method comprises the following steps: mixing the axially dihydroxy-coordinated tetravalent platinum compound and the bicyclic double-bond-containing orthoester precursor to obtain a mixture; then, adding p-toluenesulfonamide dissolved in a solvent to the mixture; finally, adding dimethyl sulfoxide, performing a reaction under nitrogen gas protection, and obtaining the tetravalent platinum compound-bicyclic double-bond-containing amphiphilic polymer prodrug after terminating the reaction.

5. The method of preparing the tetravalent platinum compound-bicyclic double-bond-containing amphiphilic polymer prodrug according to claim 4, wherein the bicyclic double-bond-containing orthoester precursor is selected from the group consisting of 4,4-dimethoxy-bis-(2-methyl-1,3-dioxolane), 3,9-dimethylene-2,4,8,10-tetraoxaspiro[5.5]undecane, (Z)-2-ethylidene-4-[(E)-2-ethylidene-1,3-dioxolan-4-yl-methoxy-methyl]-1,3-dioxolane, and 3,9-divinyl-2,4,8,10-tetraoxaspiro[5.5]undecane; and a molar ratio of the axially dihydroxy-coordinated tetravalent platinum compound to the bicyclic double-bond-containing orthoester precursor and to the p-toluenesulfonamide is 1:1:2‰.

6. The method of preparing the tetravalent platinum compound-bicyclic double-bond-containing amphiphilic polymer prodrug according to claim 4, wherein the reaction is a stirring reaction at 30° C. to 60° C. for 24 h to 72 h;
a step of terminating the reaction is dropwise adding triethylamine; and
in the p-toluenesulfonamide dissolved in the solvent, the solvent is dimethyl sulfoxide or dimethylformamide.

7. A nano-micelle formed by the tetravalent platinum compound-bicyclic double-bond-containing amphiphilic polymer prodrug according to claim 1.

8. A method of preparing the nano-micelle according to claim 7, wherein the method comprises the following steps: placing the tetravalent platinum compound-bicyclic double-bond-containing amphiphilic polymer prodrug in a dialysis bag with a molecular weight cutoff value of 3500 for a light-proof dialysis in a medium for 48-72 h, and obtaining the nano-micelle after performing a freeze-drying; and
the medium is replaced every 4 to 8 h during a process of the light-proof dialysis, and the medium is deionized water having a pH of 8 to 10 corrected with triethylamine.

9. A method of preparing an anti-tumor nano-pharmaceutical preparation, comprising: using the nano-micelle according to claim 7 as a drug carrier for preparing the anti-tumor nano-pharmaceutical preparation.

10. The method according to claim 9, further comprising the following steps: dissolving the nano-micelle in dimethyl sulfoxide or dimethylformamide, and adding a cargo to obtain a solution; after being fully dissolved, placing the solution in a dialysis bag with a molecular weight cutoff value of 3500 for a light-proof dialysis in a medium for 48-72 h, and obtaining the anti-tumor nano-pharmaceutical preparation after performing a freeze-drying; and
the cargo is one or more selected from the group consisting of an antitumor drug, an immune factor, a photosensitizer, and an interference factor; the antitumor drug is one or more selected from the group consisting of camptothecin, paclitaxel, docetaxel, doxorubicin, 5-fluorouracil, etoposide, and bleomycin; the immune factor is one or more selected from the group consisting of whey protein, lysozyme, and proline-rich polypeptide; the photosensitizer is one or more selected from the group consisting of hematoporphyrin derivative, 5-aminolevulinic acid, and m-tetrahydroxyphenyl chlorin; the interference factor is one or more selected from the group consisting of IFN-α1 type, IFN-α2 type, Rorferon-A, Wellferon and combined interferon; and the medium is replaced every 4 to 8 h during the process of light-proof dialysis, and the medium is deionized water having a pH of 8 to 10 corrected with triethylamine.

11. The method of preparing the tetravalent platinum compound-bicyclic double-bond-containing amphiphilic polymer prodrug according to claim 3, wherein $L_1$ is Cl; and $L_2$ is Cl.

12. The method of preparing the tetravalent platinum compound-bicyclic double-bond-containing amphiphilic polymer prodrug according to claim 11, wherein the method comprises the following steps: mixing the axially dihydroxy-coordinated tetravalent platinum compound and the bicyclic double-bond-containing orthoester precursor to obtain a mixture; then, adding p-toluenesulfonamide dissolved in a solvent to the mixture; finally, adding dimethyl sulfoxide, performing a reaction under nitrogen gas protection, and obtaining the tetravalent platinum compound-bicyclic double-bond-containing amphiphilic polymer prodrug after terminating the reaction.

13. The method of preparing the tetravalent platinum compound-bicyclic double-bond-containing amphiphilic polymer prodrug according to claim 12, wherein the bicyclic double-bond-containing orthoester precursor is selected from the group consisting of 4,4-dimethoxy-bis-(2-methyl-1,3-dioxolane), 3,9-dimethylene-2,4,8,10-tetraoxaspiro[5.5]undecane, (Z)-2-ethylidene-4-[(E)-2-ethylidene-1,3-dioxolan-4-yl-methoxy-methyl]-1,3-dioxolane, and 3,9-divinyl-2,4,8,10-tetraoxaspiro[5.5]undecane; and
a molar ratio of the axially dihydroxy-coordinated tetravalent platinum compound to the bicyclic double-bond-containing orthoester precursor and to the p-toluenesulfonamide is 1:1:2‰.

14. The method of preparing the tetravalent platinum compound-bicyclic double-bond-containing amphiphilic polymer prodrug according to claim 12, wherein the reaction is a stirring reaction at 30° C. to 60° C. for 24 h to 72 h;
a step of terminating the reaction is dropwise adding triethylamine; and
in the p-toluenesulfonamide dissolved in the solvent, the solvent is dimethyl sulfoxide or dimethylformamide.

15. The nano-micelle according to claim 7, wherein $L_1$ is Cl; and $L_2$ is Cl.

16. The method of preparing the nano-micelle according to claim 8, wherein $L_1$ is Cl; and $L_2$ is Cl.

17. The method of preparing an anti-tumor nano-pharmaceutical preparation according to claim 9, wherein $L_1$ is Cl; and $L_2$ is Cl.

18. The method according to claim 17, further comprising the following steps: dissolving the nano-micelle in dimethyl sulfoxide or dimethylformamide, and adding a cargo to obtain a solution; after being fully dissolved, placing the solution in a dialysis bag with a molecular weight cutoff value of 3500 for a light-proof dialysis in a medium for 48-72 h, and obtaining the anti-tumor nano-pharmaceutical preparation after performing a freeze-drying; and
the cargo is one or more selected from the group consisting of an antitumor drug, an immune factor, a photosensitizer, and an interference factor; the antitumor drug is one or more selected from the group consisting of camptothecin, paclitaxel, docetaxel, doxorubicin, 5-fluorouracil, etoposide, and bleomycin; the immune factor is one or more selected from the group consisting of whey protein, lysozyme, and proline-rich polypeptide; the photosensitizer is one or more selected from the group consisting of hematoporphyrin derivative, 5-aminolevulinic acid, and m-tetrahydroxyphenyl chlorin; the interference factor is one or more selected from the group consisting of IFN-α1 type, IFN-α2 type, Rorferon-A, Wellferon and combined interferon; and the medium is replaced every 4 to 8 h during the process of light-proof dialysis, and the medium is deionized water having a pH of 8 to 10 corrected with triethylamine.

* * * * *